United States Patent [19]

Sudilovsky et al.

[11] Patent Number: 4,931,430

[45] Date of Patent: Jun. 5, 1990

[54] METHOD FOR PREVENTING OR TREATING ANXIETY EMPLOYING AN ACE INHIBITOR

[75] Inventors: Abraham Sudilovsky, Lawrenceville; Zola P. Horovitz, Princeton, both of N.J.

[73] Assignee: E. R. Squibb & Sons, Inc., Princeton, N.J.

[21] Appl. No.: 270,872

[22] Filed: Nov. 14, 1988

Related U.S. Application Data

[63] Continuation-in-part of Ser. No. 188,827, May 2, 1988, abandoned, and a continuation-in-part of Ser. No. 132,457, Dec. 14, 1987, abandoned.

[51] Int. Cl.$^5$ .................... A61K 37/02; C07K 5/06
[52] U.S. Cl. .......................................... 514/19; 514/7; 514/89; 514/91; 514/92; 514/94; 514/171; 514/212; 514/218; 514/223.5; 514/249; 514/255; 514/278; 514/318; 514/338; 514/343; 514/409; 514/422; 514/423; 514/616; 514/693
[58] Field of Search ................ 514/7, 19, 89, 91, 92, 514/94, 171, 212, 218, 223.5, 249, 255, 278, 318, 338, 343, 409, 422, 423, 616, 693; 548/413; 260/502.5 D

[56] References Cited

U.S. PATENT DOCUMENTS

| 4,046,889 | 9/1987 | Ondetti et al. | 514/422 |
|---|---|---|---|
| 4,311,697 | 1/1982 | Krapcho | 514/17 |
| 4,311,705 | 1/1982 | Ondetti et al. | 514/422 |
| 4,316,906 | 2/1982 | Ondetti et al. | 514/422 |
| 4,337,201 | 6/1982 | Petrillo, Jr. | 548/413 |
| 4,379,146 | 4/1983 | Greenlee et al. | 548/413 |
| 4,381,297 | 4/1983 | Kavanewsky et al. | 548/413 |
| 4,423,242 | 12/1983 | Wilkinson et al. | 260/502.5 D |
| 4,452,790 | 6/1984 | Karanewsky et al. | 548/413 |
| 4,504,492 | 3/1985 | Wilkinson et al. | 514/616 |
| 4,602,002 | 7/1986 | Patchett et al. | 514/11 |
| 4,652,563 | 3/1987 | Slater | 514/19 |
| 4,652,641 | 3/1987 | Parsons . | |

FOREIGN PATENT DOCUMENTS 361039 10/1987 Fed. Rep. of Germany ........ 514/19

OTHER PUBLICATIONS

"Angiotensin Converting Enzyme Inhibitors: Animal Experiments Suggest a New Pharmacological Treatment for Alcohol Abuse in Humans", G. Spinosa et al, Alcoholism: Clinical and Experimental Research, vol. 12, No. 1, Jan./Feb. 1988, pp. 65–70.

S. J. Dolin et al, "Calcium Channel Antagonists Decrease the Ethanol Withdrawal Syndrome" British Journal of Pharm., vol. 87, Mar. Suppl. 40P (1986).

Qin Wencai et al, "Nimodipine, Nifedipine and Vincamine Improve Amnesia Induced by Anisodine and Sodium Nitrite in Rats and Mice" Chung Kuo I Hsueh Ko Hsueh Yuan Hsueh Pao, Oct. 1986, 8(5), pp. 366–370.

S. H. Croog et al, "The Effects of Antihypertensive Therapy on the Quality of Life" New Engl. J. of Med., 314:1657–1664 (6/26/86).

Primary Examiner—Lester L. Lee
Attorney, Agent, or Firm—Burton Rodney

[57] ABSTRACT

A method is provided for inhibiting onset of or treating anxiety by administering an ACE inhibitor, such as captopril, fosinopril, zofenopril or SQ 29,852, alone or in combination with a calcium channel blocker such as diltiazem or nifedipine, over a prolonged period of treatment.

36 Claims, 32 Drawing Sheets

Anxiolytic potential of captopril, zofenopril, SQ 29,852 and fosinopril following oral administration in the mouse.
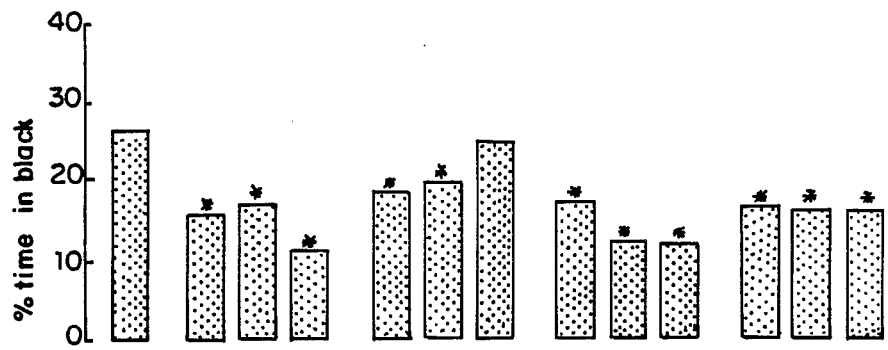
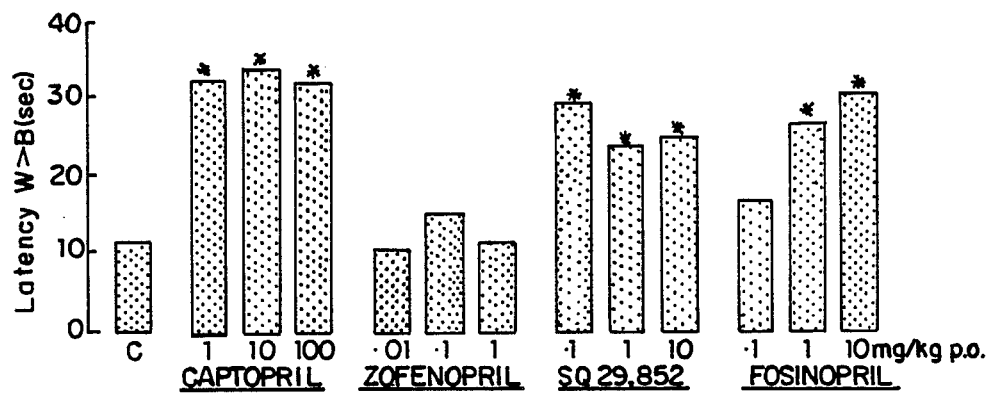
n=5. S.E.M.s<12.2% *P<0.01-P<0.001.
FIG. 7

Anxiolytic potential detected in a marmoset human threat test.
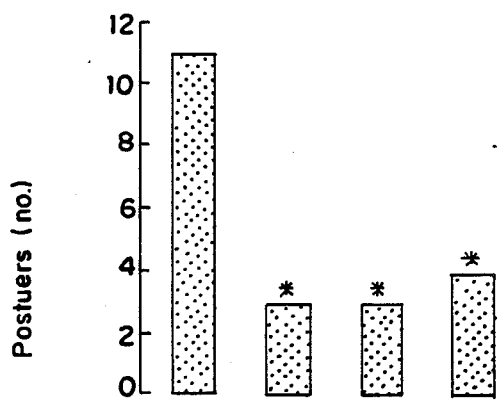
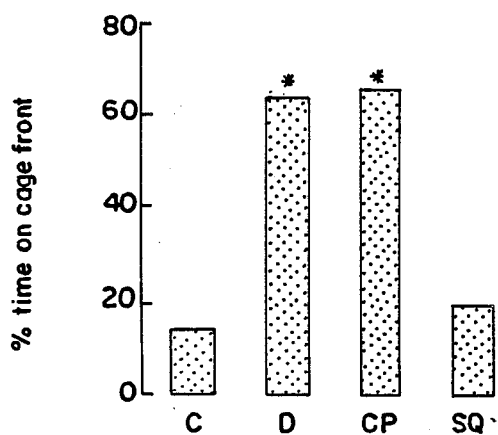
C=Vehicle control
D=Diazepam 0.25mg/kg s.c.
CP=Captopril 1.0 mg/kg s.c.
SQ=SQ 29,852 0.1mg/kg s.c.
n=4
S.E.M.s <11.7%
*P<0.001
FIG. 31

METHOD FOR PREVENTING OR TREATING ANXIETY EMPLOYING AN ACE INHIBITOR

REFERENCE TO OTHER APPLICATIONS

This is a continuation-in-part of application Ser. No. 188,827 filed May 2, 1988, now abandoned and application Ser. No. 132,457, filed Dec. 14, 1987 now abandoned.

FIELD OF THE INVENTION

The present invention relates to a method for preventing or treating anxiety by administering an ACE inhibitor, such as captopril, SQ 29,852, zofenopril, fosinopril or enalapril, alone or in combination with a calcium channel blocker, such as diltiazem, nifedipine or verapamil.

U.S. Pat. Nos. 4,046,889 and 4,105,776 to Ondetti et al discloses proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al. discloses phosphonate substituted amino or imino acids and salts thereof and covers (S)-1-[6-amino-2-[[hydroxy(4-phenylbutyl)-phosphinyl]oxy]-1-oxohexyl]-L-proline (SQ 29,852). These compounds are ACE inhibitors useful in treating hypertension.

U.S. Pat. No. 4,316,960 to Ondetti et al. discloses ether and thioether mercaptoacyl prolines which are ACE inhibitors useful in treating hypertension.

This Ondetti et al patent covers zofenopril.

DESCRIPTION OF THE INVENTION

In accordance with the present invention, a method is provided for preventing or treating anxiety in mammalian species wherein an antianxiety effective amount of an angiotensin converting enzyme inhibitor alone or in combination with a calcium channel blocker is systemically, such as orally or parenterally, administered.

The method of the invention is useful in treating or preventing anxiety including chronic and acute anxiety disorders (or anxiety and phobic neuroses) including panic disorder with or without agoraphobia, agoraphobia, social phobia, simple phobia, obsessive compulsive disorder (or obsessive compulsive neurosis), post-traumatic stress disorder, generalized anxiety disorder, anxiety disorder not otherwise specified, and mixed anxiety-depression.

In addition, the method of the invention is useful in treating or preventing anxiety associated with withdrawal from drugs of dependency and/or addiction. Thus, the method of the invention is useful in reducing anxiety and thus facilitates withdrawal from alcohol dependency, nicotine dependency, cocaine dependency and benzodiazepine dependency as well as withdrawal from other drug dependency.

Where a combination of ACE inhibitor and calcium channel blocker are to be used, the ACE inhibitor will be employed in a weight ratio to the calcium channel blocker of within the range of from about 0.1:1 to about 10:1 and preferably from about 0.4:1 to about 2.5:1.

The angiotensin converting enzyme inhibitor which may be employed herein includes substituted proline derivatives, such as any of those disclosed in U.S. Pat. No. 4,046,889 or 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in U.S. Pat. No. 4,374,829 mentioned above, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (SQ 29,852) being preferred, phosphinylalkanoyl prolines disclosed in U.S. Pat. No. 4,168,267 mentioned above with fosinopril being preferred, mercaptoacyl derivatives of substituted prolines, disclosed in U.S. Pat. No. 4,316,906 with zofenopril being preferred, any of the phosphinylalkanoyl substituted prolines disclosed in U.S. Pat. No. 4,337,201 discussed above, and the phosphonamidates disclosed in U.S. Pat. No. 4,432,971 discussed above.

Other examples of ACE inhibitors that may be employed herein include Beecham's BRL 36,378 as disclosed in European Pat. Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]amino]-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. Pat. appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4- tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives.

The above-mentioned U.S. patents are incorporated herein by reference.

The calcium antagonist which will be used herein may be diltiazem which is disclosed in U.S. Pat. No. 3,562,257 and which has the chemical name 3-(acetyloxy)-5-[2-(dimethylamino)ethyl-2,3- dihydro-2-(4-methoxyphenyl)-1,5-benzothiazepin-4(5H)-one and the structure

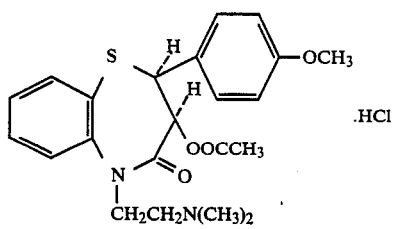

4-Phenyl-1,4-dihydropyridine calcium antagonists may be employed which will have the structure

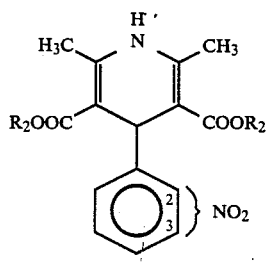

wherein $R_1$ and $R_2$ may be the same or different and are lower alkyl or lower alkoxy (lower alkyl) where lower alkyl and lower alkoxy contain 1 to 4 carbons.

The above compounds and methods for preparing same are disclosed in U.S. Pat. Nos. 3,644,627, 3,485,847, 3,488,359, 3,574,843, 3,799,934, 3,932,645 and 4,154,839 which are incorporated herein by reference.

The dihydropyridine calcium antagonist present in the composition of the invention will preferably be nifedipine, that is, the compound of formula C wherein $R_1$ is $CH_3$, $R_2$ is $CH_3$ and $NO_2$ is at the 2-position, namely,

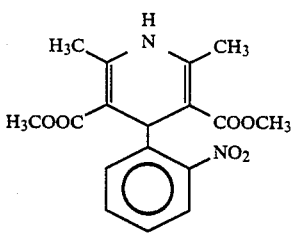

which is disclosed in U.S. Pat. Nos. 3,644,627 and 3,485,847.

Other preferred 4-phenyl-1,4-dihydropyridine calcium antagonists suitable for use herein include niludipine, that is, the compound of formula C wherein $R_1$ is —$(CH_2)_2OC_3H_7$, $R_2$ is —$(CH_2)_2OC_3H_7$ and $NO_2$ is at the 3-position (disclosed in U.S. Pat. Nos. 3,488,359 and 3,574,843); nimodipine, that is the compound of formula C wherein $R_1$ is —$(CH_2)_2OCH_3$, $R_2$ is —$CH(CH_3)_2$ and $NO_2$ is at the 3-position (disclosed in U.S. Pat. Nos. 3,799,934 and 3,932,645); nitrendipine, that is, the compound of formula C wherein $R_1$ is —$CH_2CH_3$, $R_2$ is —$CH_3$ and $NO_2$ is at the 3-position (disclosed in U.S. Pat. Nos. 3,799,934 and 3,932,645); and nisoldipine, that is, the compound of formula C wherein $R_1$ is —$CH_3$, $R_2$ is —$CH_2CH(CH_3)_2$ and $NO_2$ is at the 2-position (disclosed in U.S. Pat. Nos. 3,799,934, 3,932,645 and 4,154,839). Verapamil may also be employed.

In addition, verapamil may be employed.

The disclosure of the above-mentioned U.S. Patents are incorporated herein by reference.

In carrying out the method of the present invention, the angiotensin converting enzyme inhibitor alone or in combination with the calcium channel blocker may be administered to mammalian species, such as monkeys, dogs, cats, rats and humans, and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms such as intramuscular, intraperitoneal, or intravenous are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg alone or in combination with the calcium channel blocker in an amount within the range of from about 0.01 mg/kg to about 100 mg/kg and preferably from about 0.1 mg/kg to about 25 mg/kg with the ACE inhibitor and calcium channel blocker being employed together in the same oral dosage form or in separate oral dosage forms taken at the same time.

A preferred oral dosage form, such as tablets or capsules, will contain the ACE inhibitor in an amount of from about 0.1 to about 500 mg, preferably from about 5 to about 200 mg, and more preferably from about 25 to about 150 mg, alone or with the calcium channel blocker in an amount of from about 1 to about 350 mg, preferably from about 2 to about 200 mg, and more preferably from about 30 to about 150 mg.

For parenteral administration, the ACE inhibitor will be employed in an amount within the range of from about 0.005 mg/kg to about 10 mg/kg and preferably from about 0.01 mg/kg to about 1 mg/kg, alone or with the calcium channel blocker in an amount within the range of from about 0.005 mg/kg to about 20 mg/kg and preferably from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonfuls.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of ACE inhibitor and calcium channel blocker are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for onset of anxiety remains or the symptoms of anxiety continue. Sustained release forms of such formulations which may provide such amounts biweekly, weekly, monthly and the like may also be employed. A dosing period of at least one to two weeks are required to achieve minimal benefit.

BRIEF DESCRIPTION OF FIGURES

All of the accompanying Figures are graphs or charts of test data obtained as described in the working Examples.

FIGS. 6 and 7 show anxiolytic potentials of captopril, zofenopril, SQ 29,852 and fosinopril following oral administration on the mouse. In FIG. 6, S.E.M.s shown less than 11.3% and in FIG. 7, S.E.M.s shown less than 12.2%. In FIGS. 6 and 7, n=5. *P<0.01-P<0.001;

In FIG. 15, S.E.M.s shown less than 12.0% and in FIG. 16, S.E.M.s shown less than 12.7%. In both FIGS. 15 and 16, n=5. *P<0.05-P<0.001 (anxiolysis). +P<0.05-P<0.001 (anxiogenesis);

FIGS. 30, 31 and 32 show anxiolytic potential detected in a marmoset human threat test.

Figure 1:
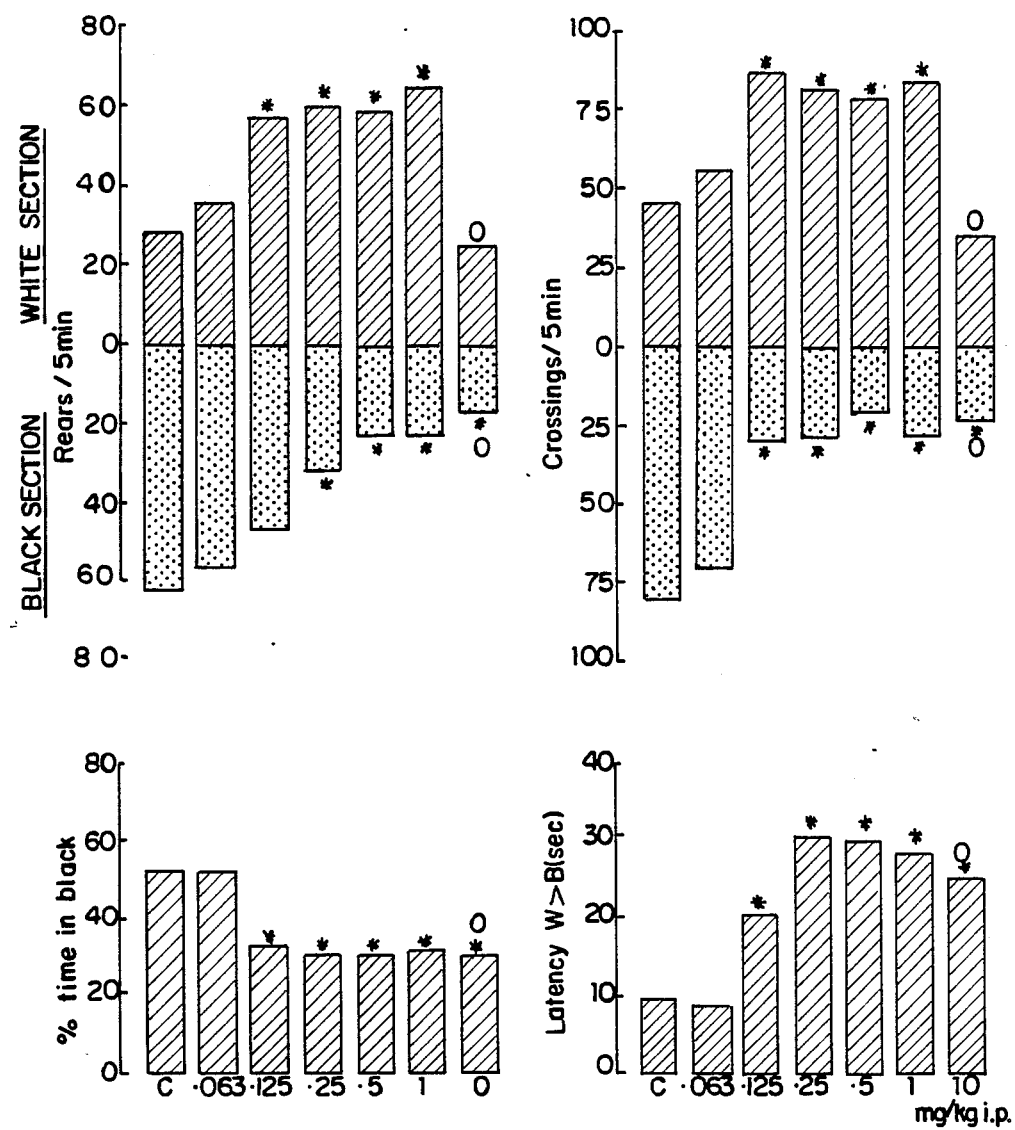
FIG. 1 shows the action of diazepam on mouse behavior in a black:white test box. n=5. S.E.M.s shown less than 12.1% *P<0.001. 0=sedation.

The following Examples represent preferred embodiments of the present invention.

EXAMPLE 1

A captopril formulation suitable for oral administration in inhibiting onset of or treating anxiety is set out below.

1000 tablets each containing 100 mg of 1-[(2S)-3-mercapto-2-methylpropionyl]-L-proline were produced from the following ingredients.

| | |
|---|---|
| 1-[(2S)-3-Mercapto-2-methylpropionyl]-L-proline (captopril) | 100 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting onset of or treating anxiety.

EXAMPLE 2

By substituting 100 g of 1-(3-mercapto-2-D-methylpropanoyl)-L-proline for the captopril in Example 1, 1000 tablets each containing 100 mg of the 1-(3-mercapto-2-D-methylpropanoyl)-L-proline are produced which is useful in inhibiting onset of or treating anxiety.

EXAMPLE 3

1000 tablets each containing 200 mg of captopril are produced from the following ingredients:

| | |
|---|---|
| Captopril | 200 g |
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in inhibiting onset of or treating anxiety.

EXAMPLE 4

Two piece #1 gelatin capsules each containing 250 mg of captopril are filled with a mixture of the following ingredients:

| | |
|---|---|
| Captopril | 250 mg |
| Magnesium stearate | 7 mg |
| USP lactose | 193 mg |

The resulting capsules are useful in inhibiting onset of or treating anxiety.

EXAMPLE 5

An injectable solution for use in inhibiting onset of or treating anxiety is produced as follows:

| | |
|---|---|
| Captopril | 500 mg |
| Methyl paraben | 5 mg |
| Propyl paraben | 1 mg |
| Sodium chloride | 25 g |
| Water for injection qs. | 5 l. |

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 6

Tablets for use in inhibiting onset of or treating anxiety are prepared as described in Example 1 except that N-(1-ethoxycarbonyl-3-phenylpropyl)-L-alanyl-L-proline (enalapril) is used in place of captopril.

EXAMPLE 7

An injectable for use in inhibiting onset of or treating anxiety is prepared as described in Example 5 except that N-(1-ethoxycarbonyl-3-phenylpropyl)-L-alanyl-L-proline (enalapril) is employed in place of captopril.

EXAMPLE 8

A zofenopril formulation suitable for oral administration in inhibiting onset of or treating anxiety is set out below.

1000 tablets each containing 100 mg of zofenopril are produced from the following ingredients.

| | |
|---|---|
| [1(S),4(S)-1-3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting onset of or treating anxiety.

EXAMPLE 9

By substituting 100 g of fosinopril for the zofenopril in Example 8, 1000 tablets each containing 100 mg of the fosinopril are produced which is useful in inhibiting onset of or treating anxiety.

EXAMPLE 10

1000 tablets each containing 200 mg of fosinopril are produced from the following ingredients:

| | |
|---|---|
| Fosinopril | 200 g |
| Lactose | 100 g |
| Avicel | 150 g |
| Corn starch | 50 g |
| Magnesium stearate | 5 g |

The fosinopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in inhibiting onset of or treating anxiety.

EXAMPLE 11

Tablets for use in inhibiting onset of or treating anxiety are prepared as described in Example 1 except that 1-[N-[hydroxy(4-phenylbutyl)phosphinyl]-L-alanyl-L-proline, disodium salt (prepared as described in U.S. Pat. No. 4,432,971) is used in place of captopril.

EXAMPLE 12

An injectable for use in inhibiting onset of or treating anxiety is prepared a described in Example 5 except that 1-[N-[hydroxy(4-phenylbutyl)phosphinyl]-L-alanyl-L-proline, disodium salt (prepared as described in U.S. Pat. No. 4,432,971) is used in place of captopril.

EXAMPLE 13

A captopril-diltiazem formulation suitable for oral administration in the treatment of anxiety is set out below.

1000 tablets each containing 100 mg of 1-[(2S)-3-mercapto-2-methylpropionyl]-L-proline and 100 mg of diltiazem are produced from the following ingredients:

| | |
|---|---|
| 1-(2S)-3-mercapto-2-methylpropionyl]-L-proline (captopril) | 100 g |
| Diltiazem | 100 g |
| Corn starch | 50 g |
| Gelatin | 7.5 g |
| Avicel (microcrystalline cellulose) | 25 g |
| Magnesium stearate | 2.5 g |

The captopril, diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 200 mg of active ingredients which is used for preventing or treating anxiety.

EXAMPLE 14

By substituting 100 g of 1-(3-mercapto-2-D-methylpropanoyl)-L-proline for the captopril in Example 13, 1000 tablets each containing 100 mg of the 1-(3-mercapto-2-D-methylpropanoyl)-L-proline and 100 mg diltiazem are produced which is useful in preventing or treating anxiety.

EXAMPLE 15

1000 tablets each containing 200 mg of captopril and 200 mg nifedipine are produced from the following ingredients:

| | |
|---|---|
| Captopril | 200 g |
| Nifedipine | 200 g |
| Lactose | 100 g |
| Avicel | 150 g |
| Corn starch | 50 g |
| Magnesium stearate | 5 g |

The captopril, nifedipine, lactose and Avicel are admixed, then blended with the corn starch. Magnesium stearate is added. The dry mixture is compressed in a tablet press to form 1000 505 mg tablets each containing 200 mg of each active ingredient. The tablets are coated with a solution of Methocel E 15 (methyl cellulose) including as a color a lake containing yellow #6. The resulting tablets are useful in preventing or treating anxiety.

EXAMPLE 16

Two piece #1 gelatin capsules each containing 250 mg of enalapril and 150 mg of nitrendipine are filled with a mixture of the following ingredients:

| | |
|---|---|
| Enalapril | 250 mg |
| Nitrendipine | 150 mg |
| Magnesium stearate | 7 mg |
| USP lactose | 193 mg |

The resulting capsules are useful in preventing or treating anxiety.

EXAMPLE 17

An injectable solution for use in treating or preventing anxiety is produced as follows:

| | |
|---|---|
| Captopril | 500 mg |
| Diltiazem | 300 mg |
| Methyl paraben | 5 g |
| Propyl paraben | 1 g |
| Sodium chloride | 25 g |
| Water for injection qs. | 5 L. |

The captopril, diltiazem, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 18

Tablets for use in preventing or treating anxiety are prepared as described in Example 13 except that N-(1-ethoxycarbonyl-3-phenylpropyl)-L-alanyl-L-proline (enalapril) is used in place of captopril and nifedipine is used in place of diltiazem.

EXAMPLE 19

Tablets for use in treating or preventing anxiety are prepared following the procedure of Example 13 except that zofenopril is employed in place of captopril and nisoldipine is used in place of diltiazem.

EXAMPLE 20

Tablets for use in treating or preventing anxiety are prepared following the procedure of Example 13 except that fosinopril is employed in place of captopril.

EXAMPLE 21

Tablets for use in treating or preventing anxiety are prepared following the procedure of Example 13 except that alacepril is employed in place of captopril.

EXAMPLE 22

Tablets for use in treating or preventing anxiety are prepared following the procedure of Example 13 except that (S)-1-[6-amino-2-[[hydroxy-(4-phenylbutyl)phosphinyl]oxy]-1-oxohexyl]-L-proline or lisinopril is employed in place of captopril.

EXAMPLE 23

Captopril, SQ 29,852, fosinopril and zofenopril, and diazepam (as a positive control) were tested for their anti-anxiety effect in the mouse black:white test box employing the following test procedure.

The mouse black:white test box (test of anxiolytic potential using mouse aversion to a brightly lit, white environment)

The studies used naive male albino BKW mice, 25-30 g. Ten mice were normally housed in each cage with free access to food and water. The mice were kept on a 12 hours light-dark cycle with lights off at 10.00 hour.

For assessment of anxiety responding animals were taken in a dark container from a dark holding room to the dimly lit testing room where the experiments were conducted between 13:00 and 18:00 hours. The apparatus used for the detection of changes in anxiety consisted of an open-topped box (45×27×27 cm high) having a smaller portion painted black (40% of area) and illuminated under a dim red light (1×60W) and partitioned from the remainder of the box which was painted white and brightly illuminated with a 60W white light source located 17 cm above the box. The floor area was lined into 9 cm squares. Access between these areas was enabled by means of a 7.5×7.5 cm opening located at floor level in the center of the partition. Animals that had received drug or vehicle injections were placed individually into the center of the white area and their behavior observed over a 5 minute period by remote video recording. An increased exploratory activity (rearings, line crossings) in the brightly-lit environment was taken as an index of anxiolytic action when a dark environment was simultaneously available. Anxiolytic activity was also associated with a delayed latency to move from the white to the black environment and a reduced % of time spent in the black environment. Thus, four behavioral parameters were noted every minute, the number of exploratory rearings in the white and black areas, the number of line crossings in the white and black areas, the latency to move from the white to the black area, and the % of time spent in the black area. Experimenters remained blind to drug treatment throughout, the code only being broken after analysis was complete.

Animals were used on a single occasion only, in experimental groups of 5 (n=5). Vehicle treated controls were run on each day of testing. Testing was carried out both after intraperitoneal (i.p.) and oral (p.o.) dosing. Where time courses of drug action were assessed, fresh groups of animals were used on each test occasion. To determine whether drug effects were maintained on subchronic treatment mice were dosed twice daily (b.d.) for 6 days and then tested 45 or 60 minutes after administration of the last dose (see below). To determine whether anxiogenesis or other adverse effects developed on withdrawal of subchronic treated twice daily with drug for 6 days then assessed in the black:-white box 24 hours after drug withdrawal (withdrawal effects, or lack of, were confirmed by testing further groups of mice 48 hours and 96 hours after withdrawal of drug).

Throughout the studies diazepam (Roche) was used as the positive control. Preparation was in minimum PEG made up to volume with distilled water (route i.p., pretreatment 60 minutes). Captopril (route i.p., pretreatment 45 minutes), fosinopril (route i.p., pretreatment 60 minutes), SQ 29,852 (route i.p., pretreatment 60 minutes), enalapril (route p.o., pretreatment 2 hours), lisinopril (route p.o., pretreatment 2 hours) and epicaptopril (route p.o., pretreatment 2 hours) were prepared in distilled water. Zofenopril (route i.p., 60 minutes pretreatment) was prepared in phosphate buffer, pH 6.0). Hydergine (commercial preparation, route p.o., pretreatment 60 minutes) was prepared as a suspension in 0.1% carboxymethylcellulose.

Results

Diazepam caused changes in mouse responding consistent with an anxiolytic potential at doses of 0.125-1 mg/kg i.p. Sedation developed at 10 mg/kg. The anxiolytic action was characterized by increased exploratory rearings and line crossings in the white section of the test box, with corresponding reductions in the white, reduced % of time spent in the black, and delayed latency to move from the white to the black compartment (FIG. 1).

Figure 2:
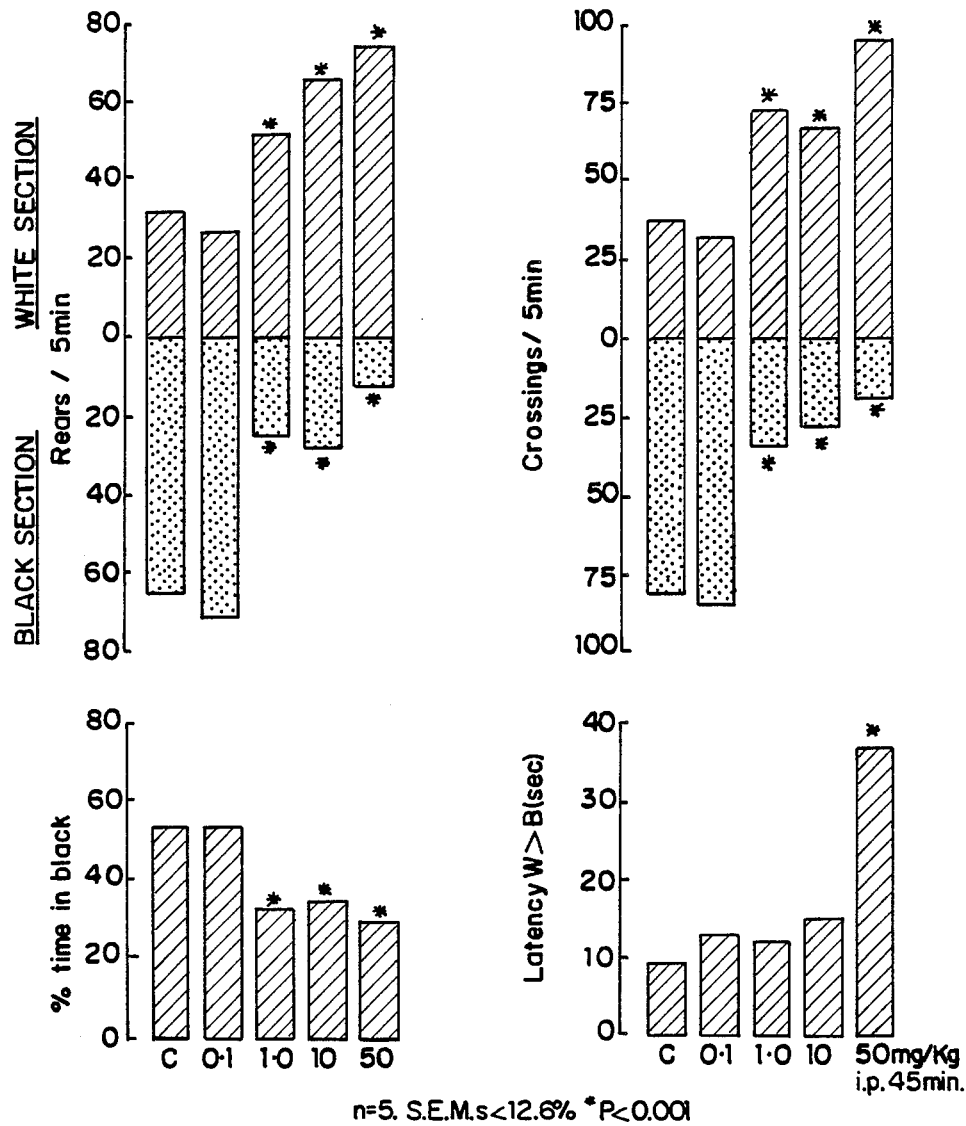
FIG. 2 shows the action of captopril on mouse behavior in the black:white test box. n=5. S.E.M.s shown less than 12.6%. *P<0.001.
Figure 3:
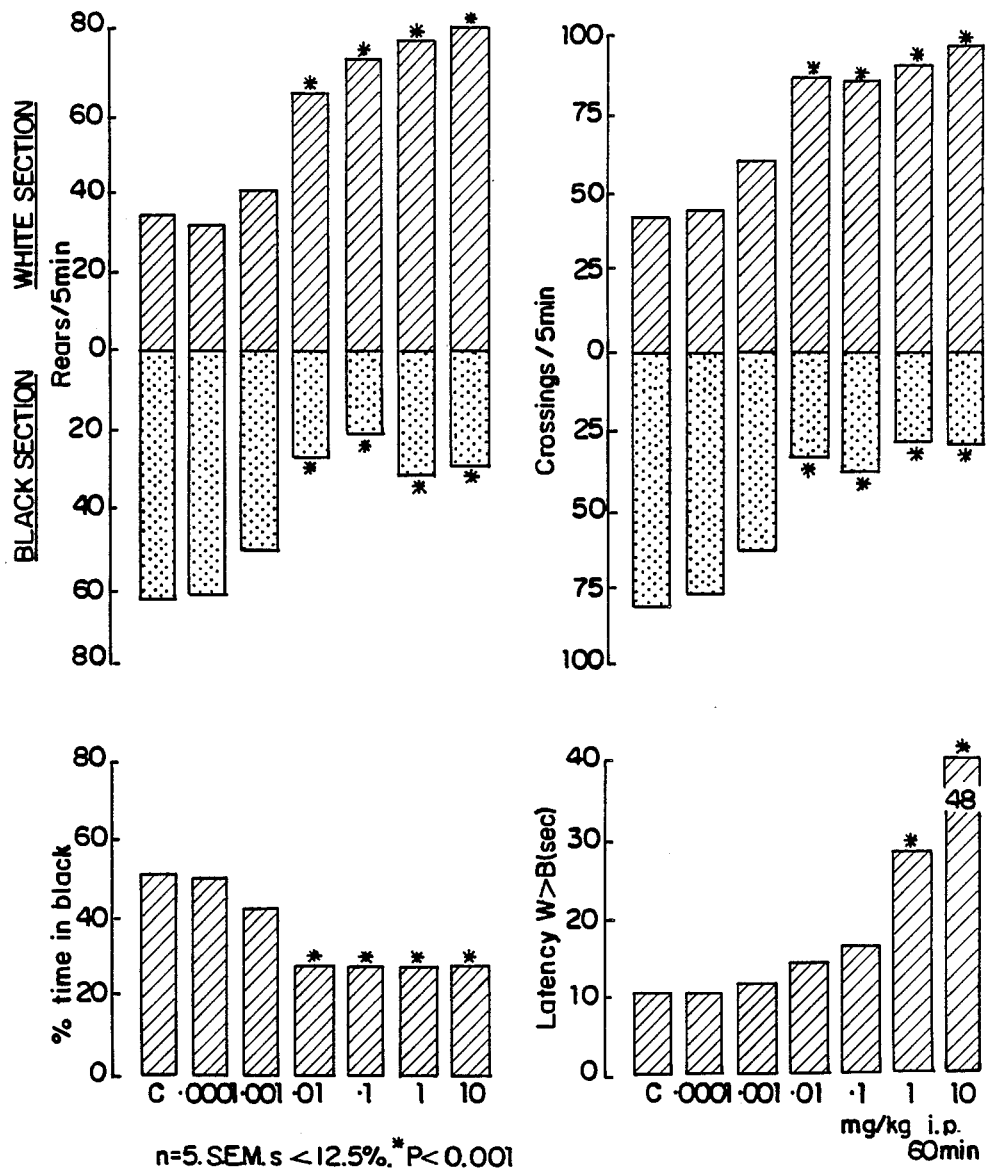
FIG. 3 shows the action of SQ 29,852 on mouse behavior in the black:white test box. n=5. S.E.M.s shown less than 12.5%. *P<0.001.
Figure 4:
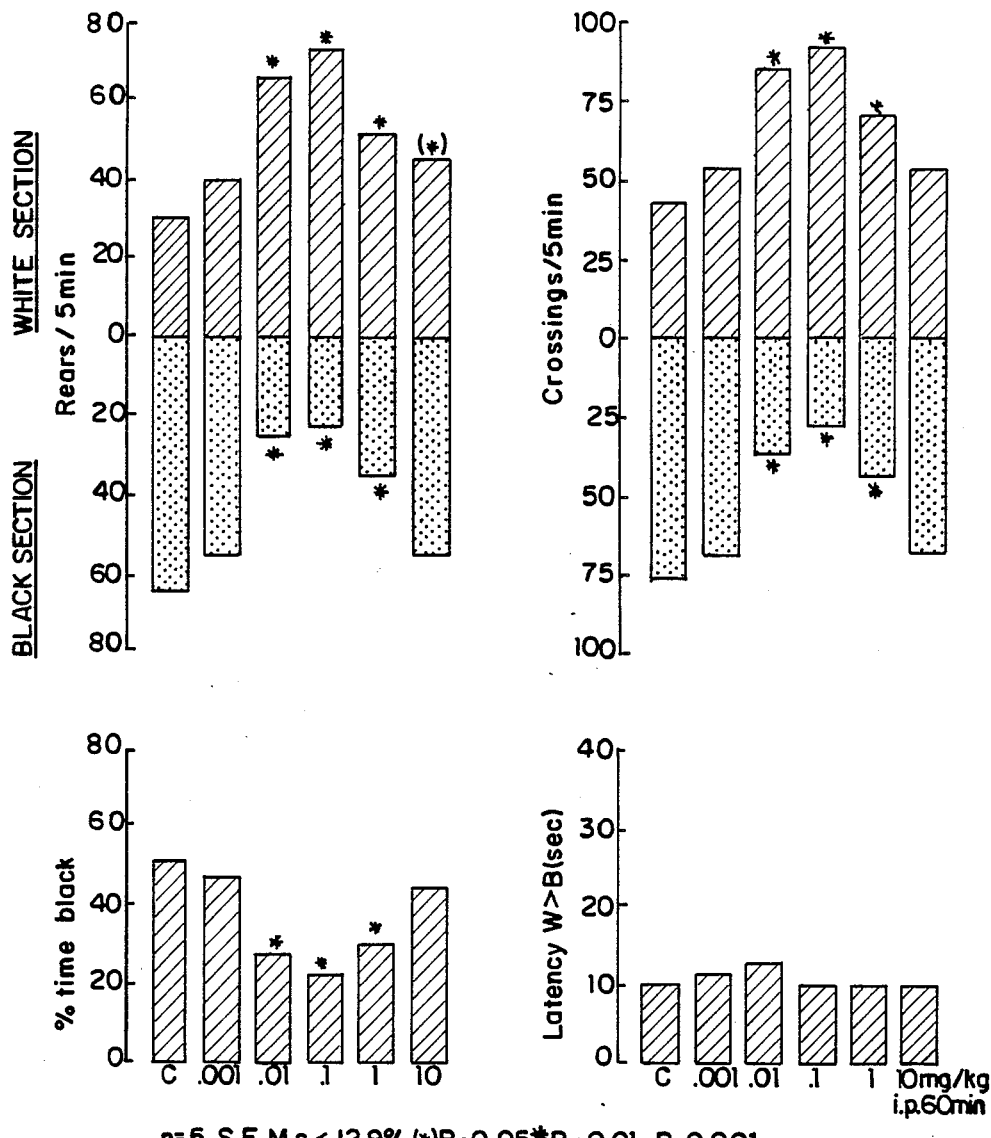
FIG. 4 shows the action of fosinopril on mouse behavior in the black:white test box. n=5. S.E.M.s shown less than 12.9%. [*]P<0.05, *P<0.01-P<0.001.

Captopril caused a similar change in behavior a recorded for diazepam but at somewhat higher doses (1-50 mg/kg i.p.) and without sedation at the highest dose (FIG. 2). Similarly, treatment with SQ 29,852 lead to increased rearings and line crossings in the white, normally averse, environment, with corresponding reductions in the black, and reduced % of time spent in the black, and delayed latency to move to the black. The latter parameter changed significantly at doses of 1 and 10 mg/kg, but other parameters significantly changed in the dose range 0.01-10 mg/kg (FIG. 3). The characteristic redistribution of exploratory rearings and line crossings was seen at 0.01-1 mg/kg fosinopril. These characteristics of anxiolytic potential were also reflected in reduced % time spent in the black environment although, surprisingly, the latency to move from the black to the white environment was never changed by fosinopril treatment (FIG. 4). Also, as the dose of fosinopril was increased so the anxiolytic potential decreased (FIG. 4).

Figure 5:
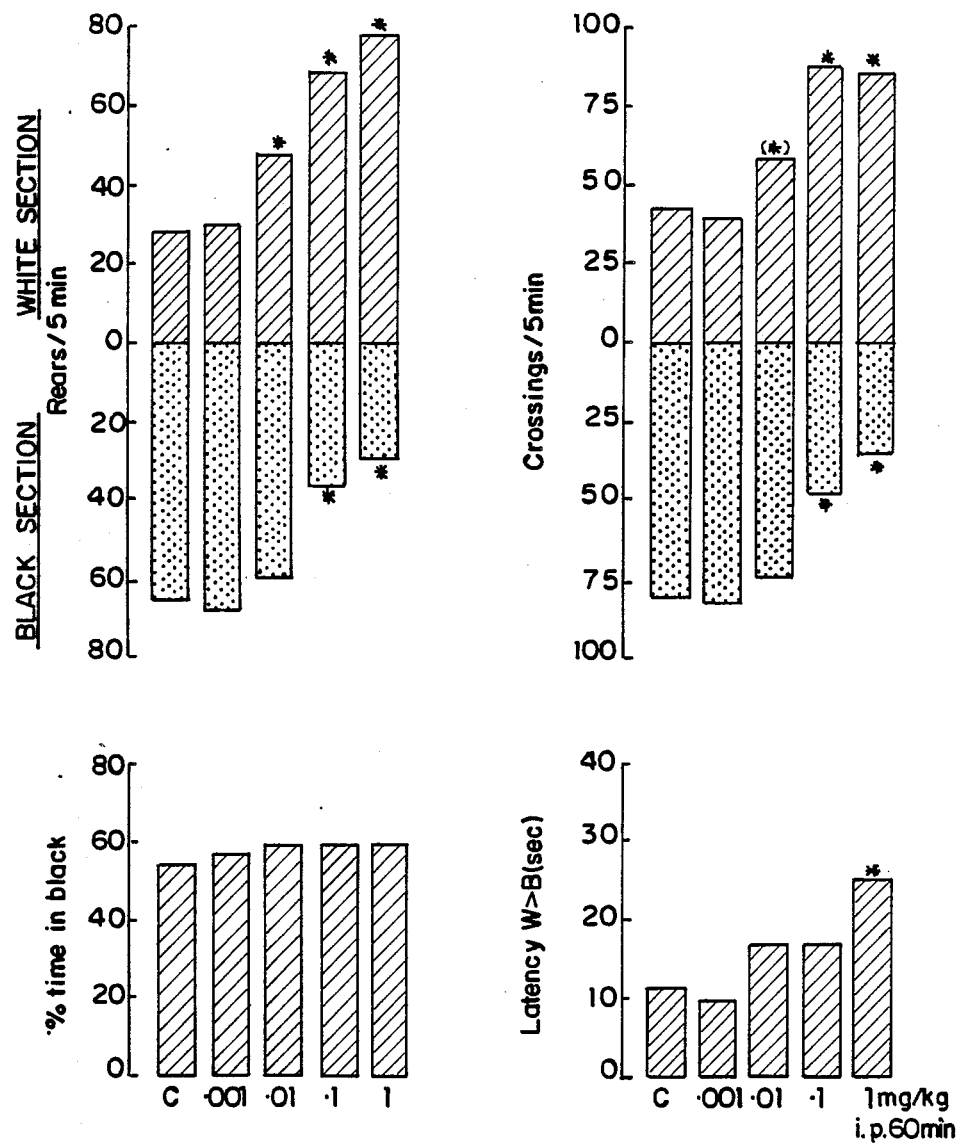
FIG. 5 shows the action of zofenopril on mouse behavior in the black:white test box. n=5. S.E.M.s shown less than 13.1%. [*]P<0.05, *P<0.01-P<0.001.

Zofenopril altered exploratory rearings and line crossings in a manner characteristic of anxiolytic agents at doses of 0.1-1.0 mg/kg (problems in drug preparation precluded the use of higher doses) but % time in black remained unchanged and latency to move from the white to the black compartment was delayed only by the highest dose of 1 mg/kg i.p. zofenopril (FIG. 5).

Figure 6:
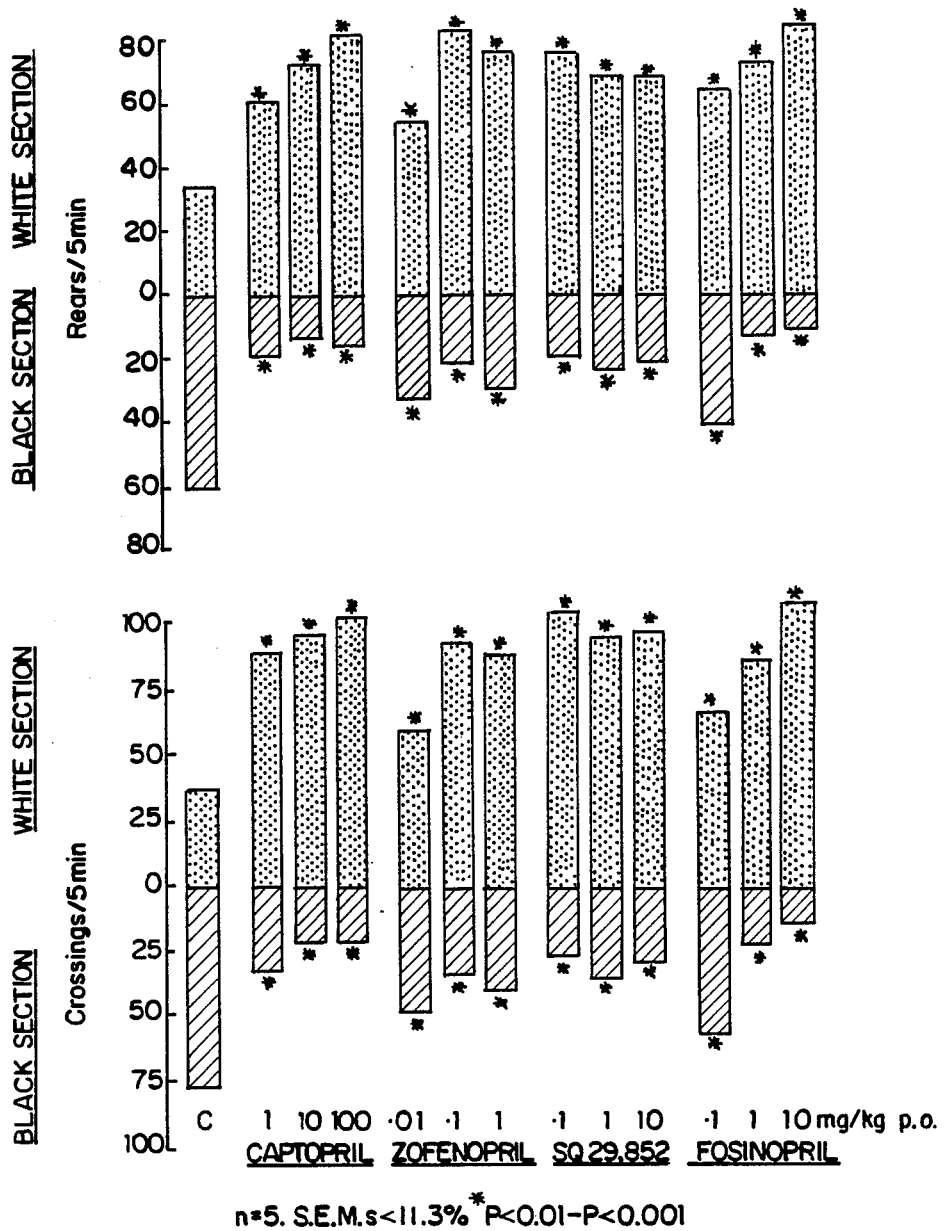

The anxiolytic actions of captopril, zofenopril, SQ 29,852 and fosinopril were maintained on oral treatment. Thus, aversion to the white, brightly lit environment was reduced by captopril (1-100 mg/kg), zofenopril (0.01-1 mg/kg), SQ 29,852 (0.1-10 mg/kg) and fosinopril (0.1-10 mg/kg) given orally (FIGS. 6 and 7). The failure of zofenopril to influence latency to move from the white to the black area on systemic injection was again seen on oral administration (FIG. 7).

Figure 8:
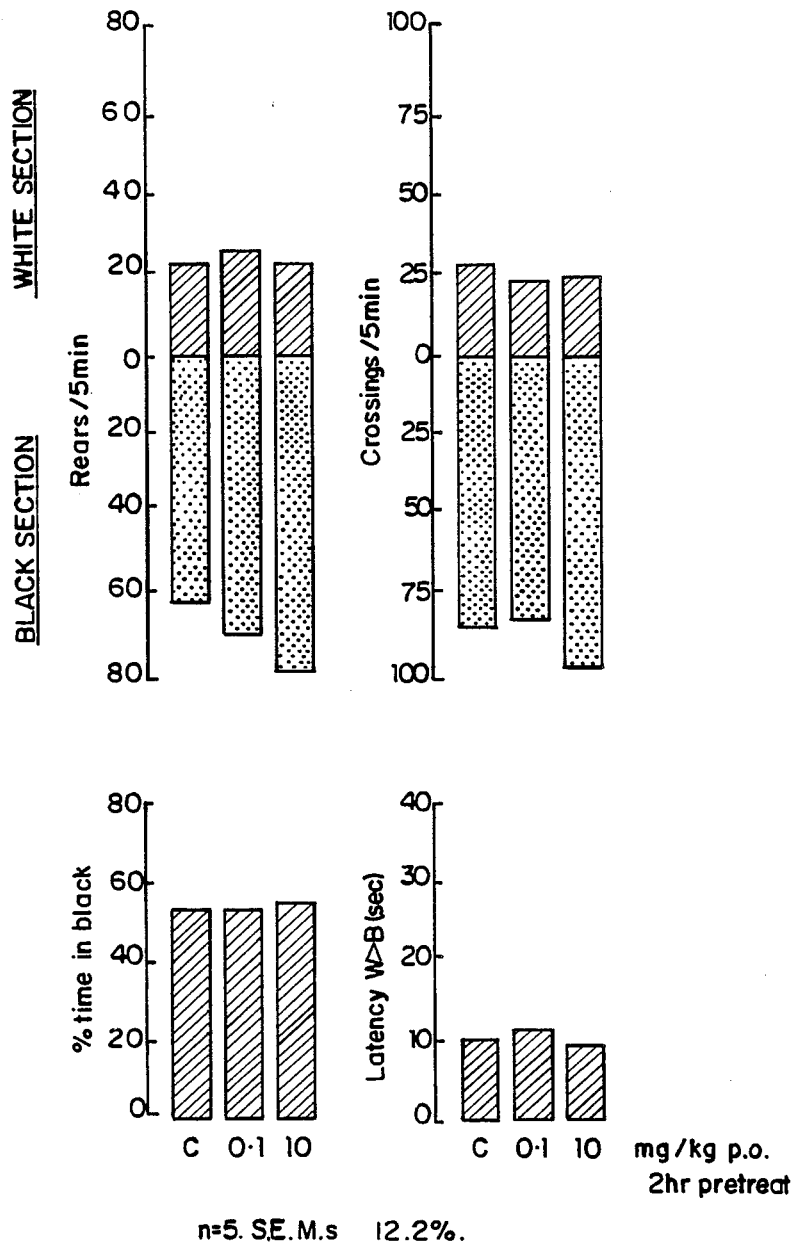
FIG. 8 shows action of epicaptopril on mouse behavior in the black:white test box. n=5. S.E.M.s shown less than 12.2%.

In contrast to captopril, SQ 29,852, zofenopril and fosinopril, epicaptopril failed to modify behavior of mice in the black:white test box. In this test, and this species, therefore, epicaptopril would appear to be devoid of anxiolytic potential (FIG. 8).

Figure 9:
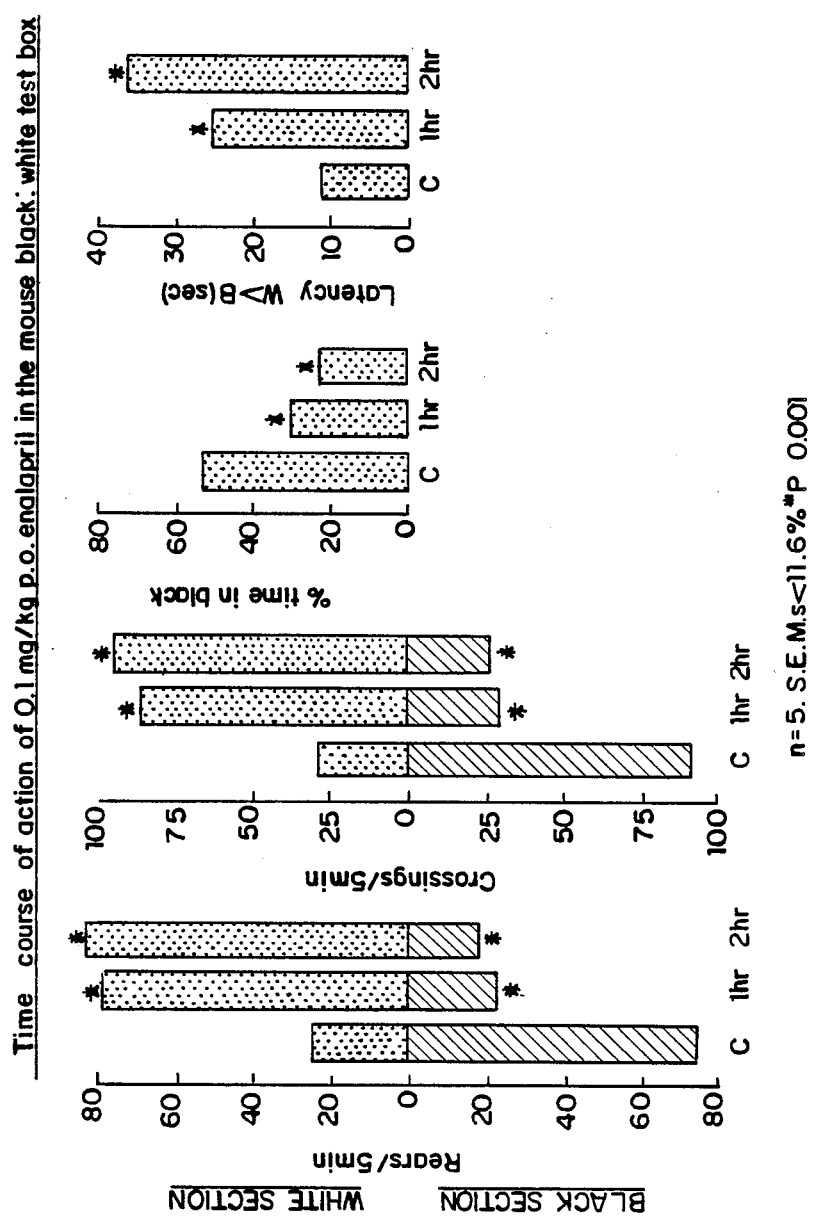
FIGS. 9 and 10 show action of enalapril on mouse behavior in the mouse black:white test box. n=5. For FIG. 9, S.E.M.s shown less than 11.6%. *P<0.001. For FIG. 10, S.E.M.s shown less than 10.3%. *P<0.001.
Figure 10:
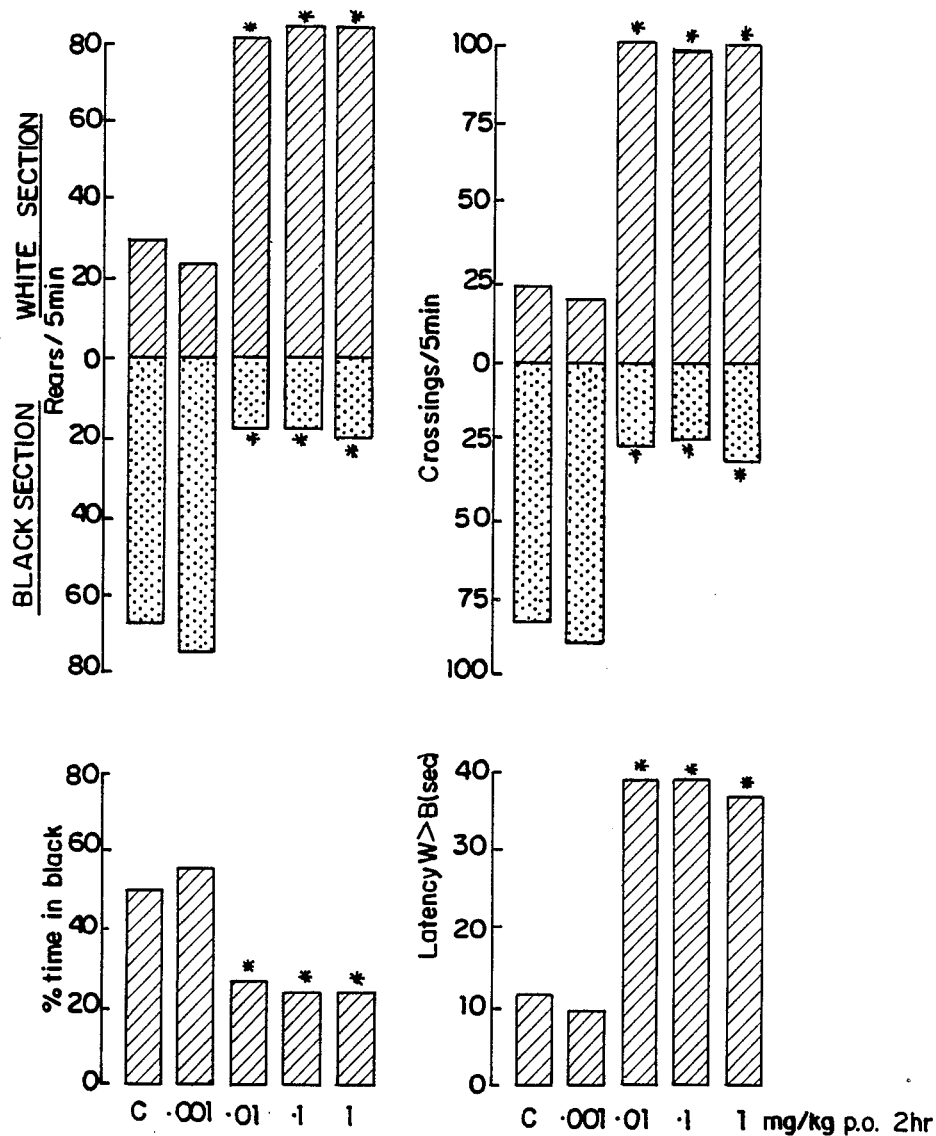
Figure 11:
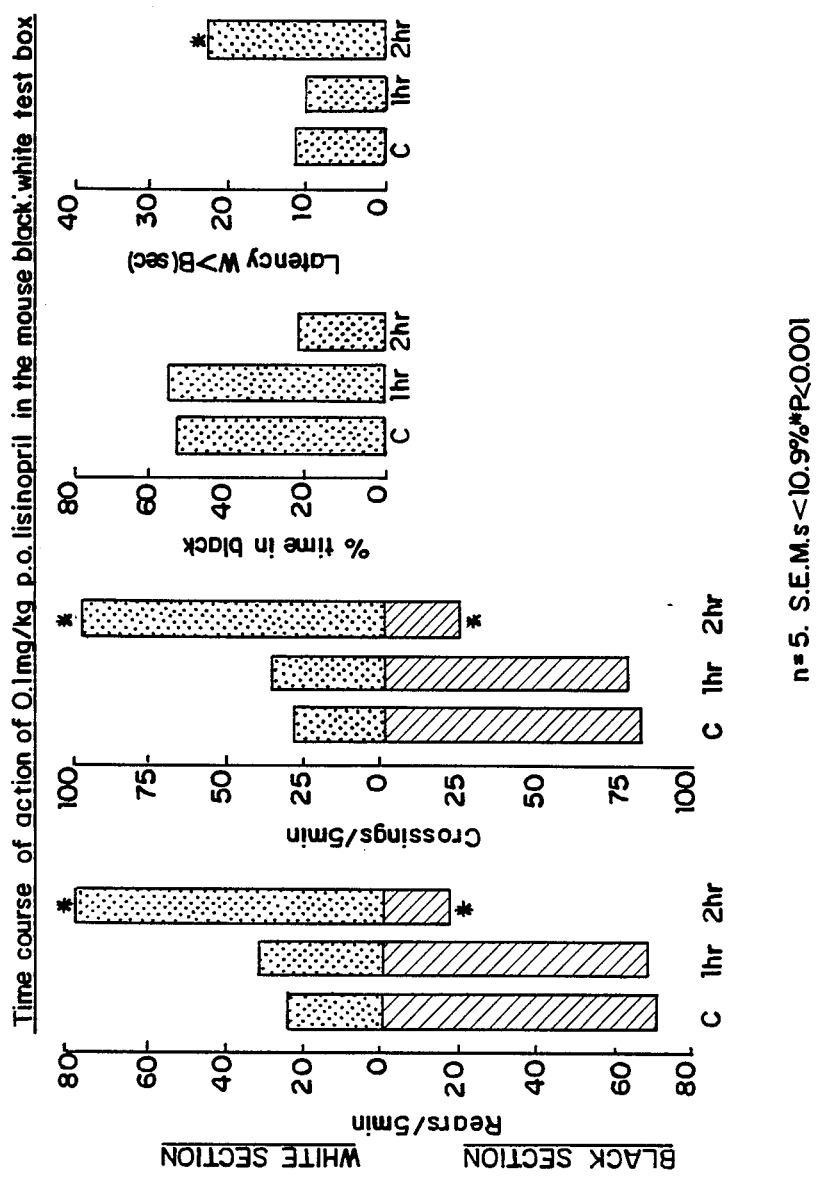
FIGS. 11 and 12 show the action of lisinopril on mouse behavior in the black:white test box. n=5. For FIG. 11, S.E.M.s shown less than 10.9%. *P<0 001. For FIG. 12, S.E.M.s shown less than 11.2%. *P<0 001.
Figure 12:
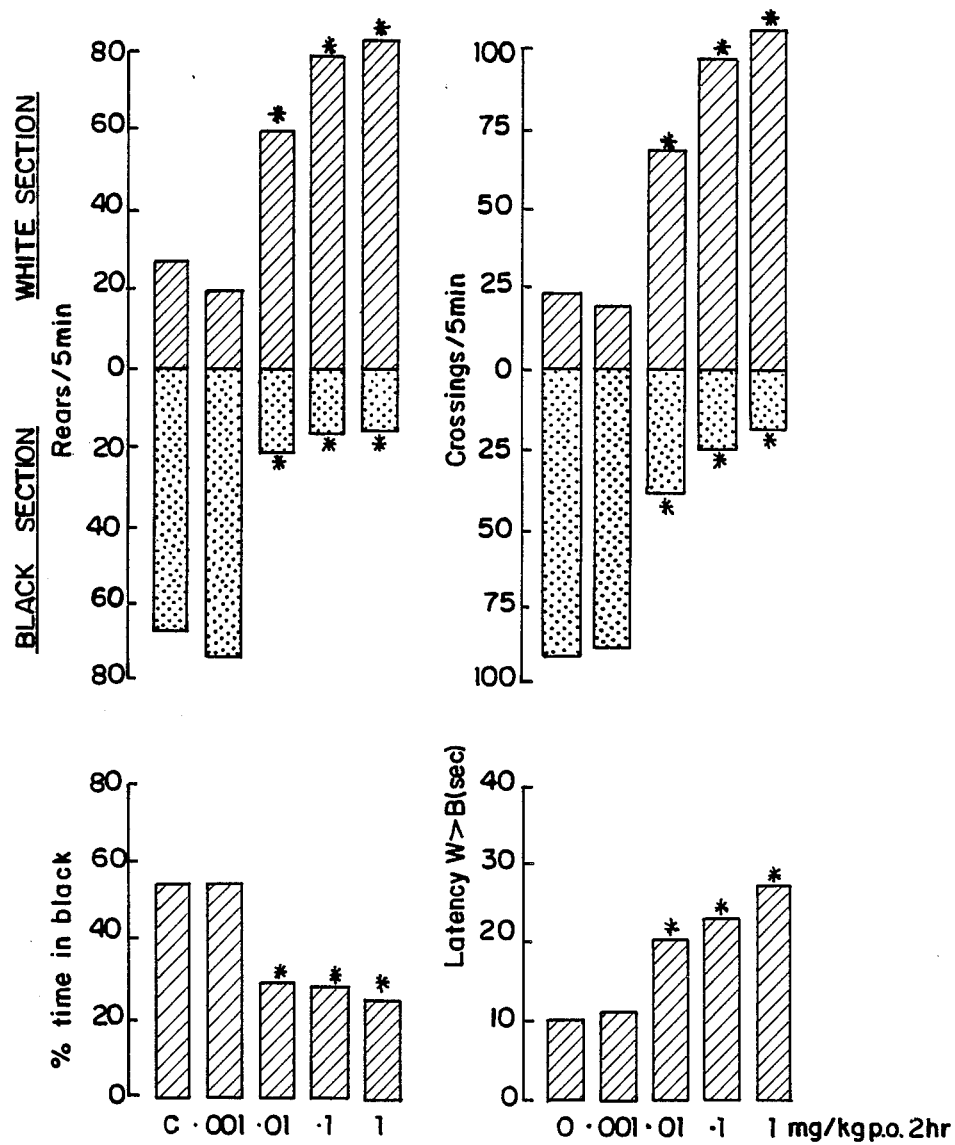

Enalapril was given orally and different groups of mice assessed 1 hour and 2 hours after treatment. A maximal anxiolytic potential was apparent at both times (FIG. 9). The onset of action of enalapril is therefore less than 1 hour, but maximal activity is maintained at 2 hours and the full dose-response curve for enalapril was therefore carried out at 2 hours. The dose-response curve for enalapril was steep, with maximal anxiolytic action apparent at doses of 0.01-1 mg/kg p.o. (seen as increased rears in the white, increased line crossings in the white, reduced % time in the black and markedly delayed latencies to move from the white) (FIG. 10). The threshold dose for enalapril was approximately 0.005 mg/kg and this was given twice daily in the habituation test (see later). Using this treatment regime over 7 days an anxiolytic potential was seen in only 1–2 animals after longer treatment.

In contrast to enalapril, the onset of action of lisinopril was delayed for 2 hours: at this time the anxiolytic action was maximum. A dose-response analysis carried out after 2 hour pretreatments showed lisinopril to be approximately equipotent to enalapril. Again, in subsequent habituation tests the threshold dose was found to be 0.005 mg/kg and, again, there was some accumulation of effect in 1 to 2 animals where an anxiolytic potential developed after 5–7 days of treatment with 0.005 mg/kg p.o. b.d.

Figure 13:
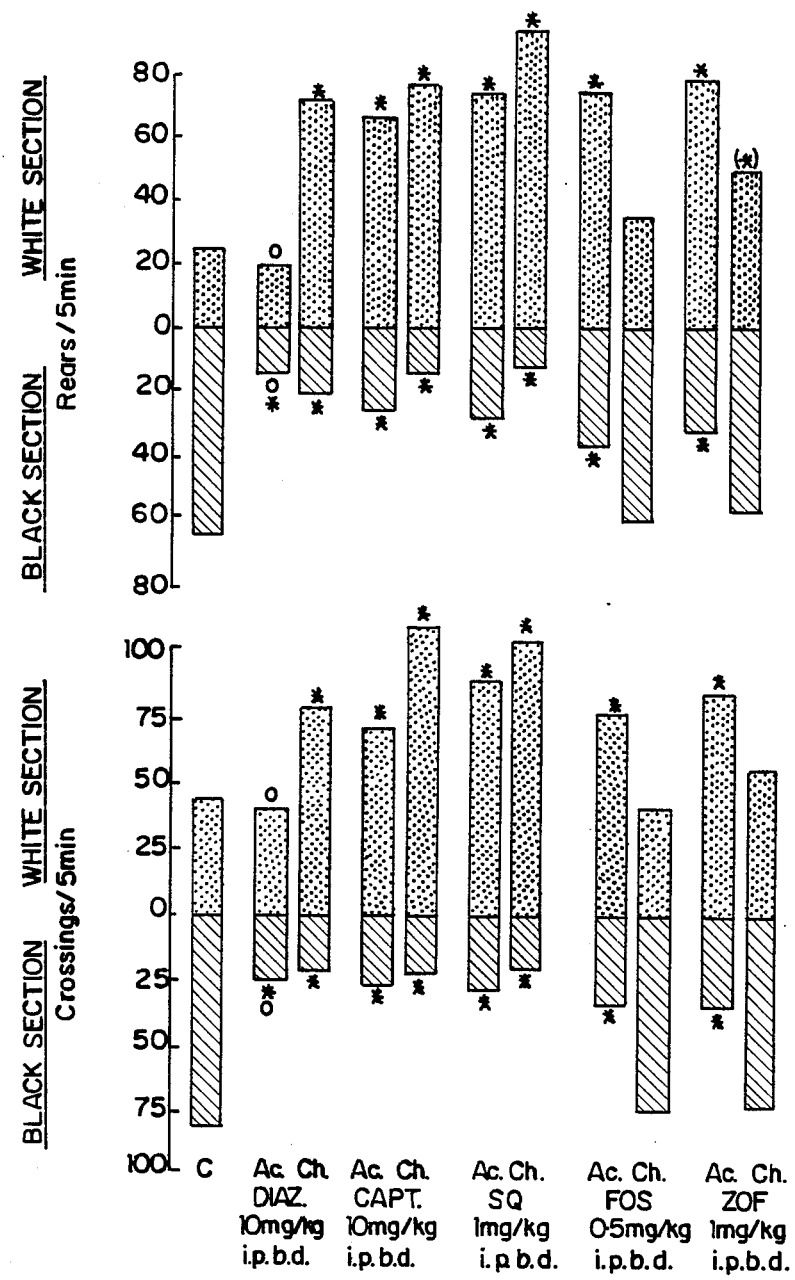
FIGS. 13 and 14 show anxiolytic potential of ACE inhibitors on subchronic treatment assessed in the mouse black:white test box. n=5. [*]P<0.05. *P<0.01-P<0.01-P<0.001. S.E.M.s shown less than 12.0% in FIG. 13 and less than 11.6% in FIG. 14. 0=Sedation.
Figure 14:
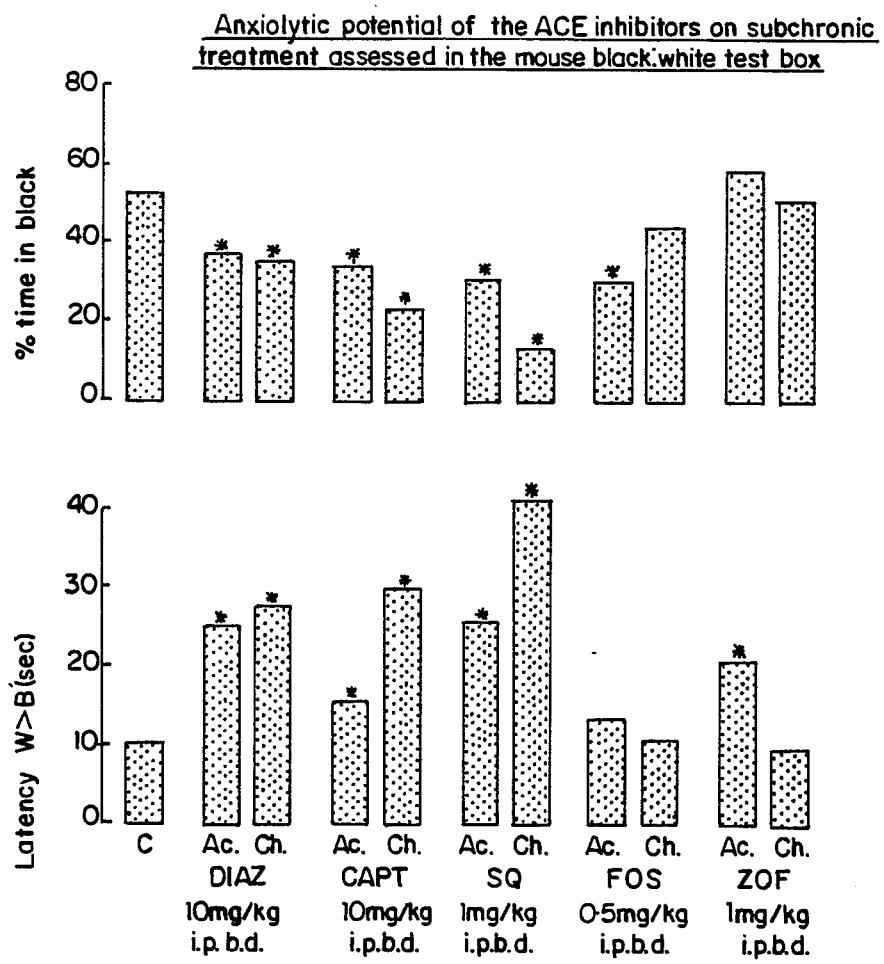
Figure 15:
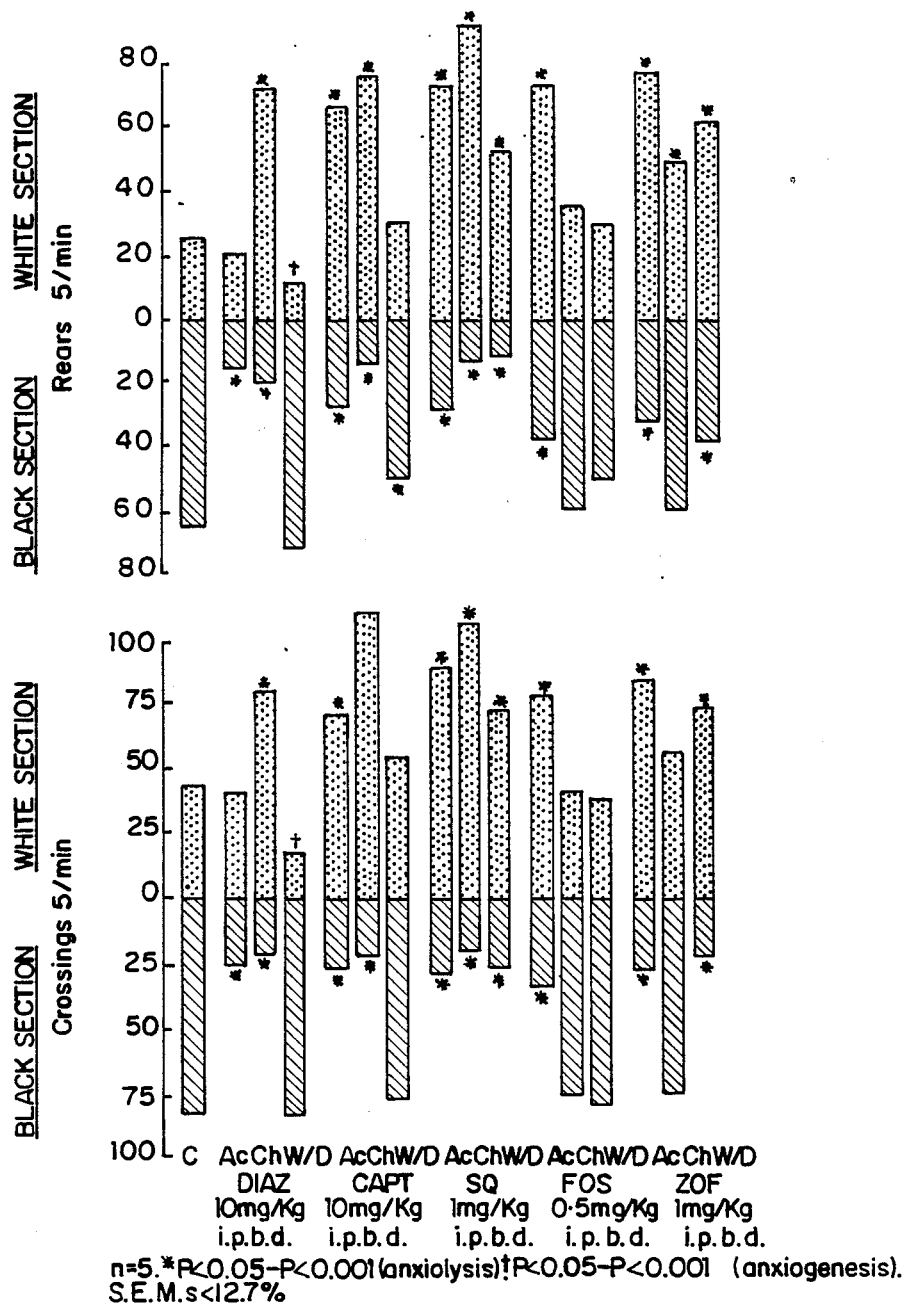
FIGS. 15 and 16 show anxiolytic potential of the ACE inhibitors on subchronic treatment and effects of abrupt withdrawal assessed in the mouse black:white test box. Treatment time 6 days, b.d. withdrawn 24 hours.
Figure 16:
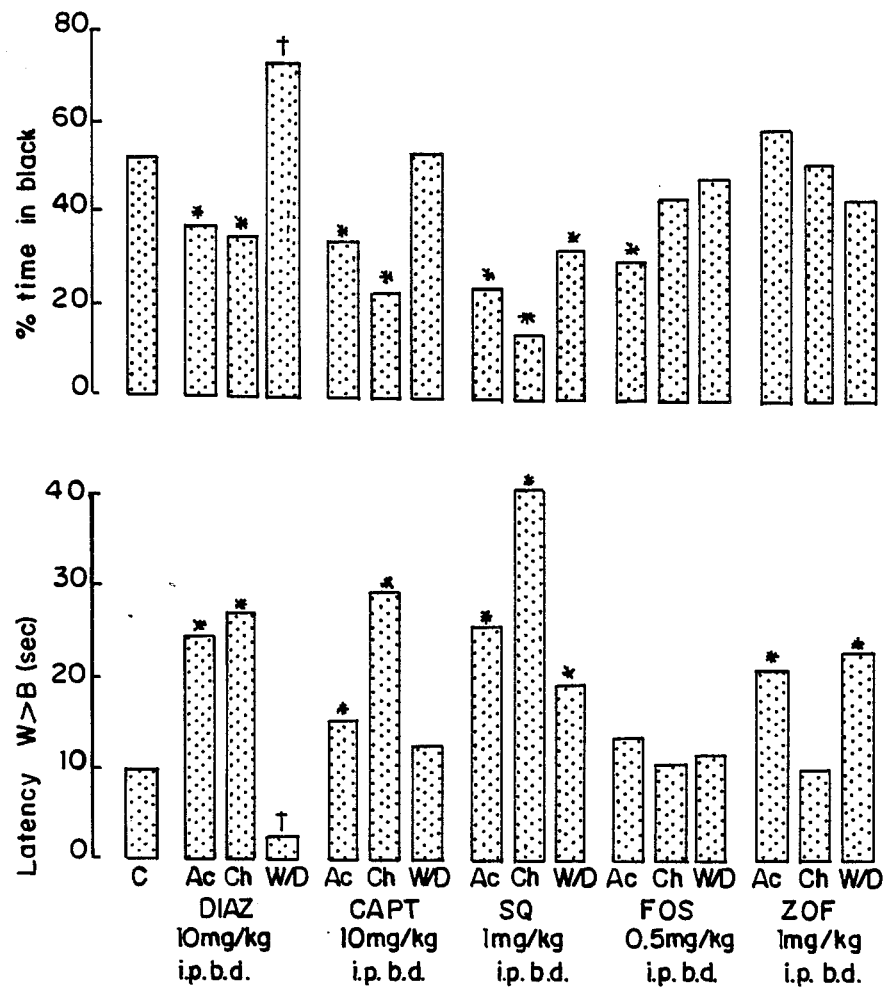

In subsequent studies captopril, SQ 29,852, fosinopril and zofenopril were given b.d. for 6 days, and comparisons of anxiolytic potential made with diazepam. The anxiolytic actions of captopril and SQ 29,852 were maintained on sub-chronic treatment whilst those of fosinopril and zofenopril waned (FIGS. 13 and 14). Testing was done 45 minutes after last dose (captopril) or 60 minutes (other ACE inhibitors and diazepam). On withdrawal from subchronic treatment with diazepam (10 mg/kg i.p. b.d. 6 days) an anxiogenesis develops (characterized by increased exploratory rears in the black, increased line crossings in the black, increased % time in the black, and reduced latency to move from the white to the black compartment, FIGS. 15 and 16). In contrast, the mice withdrawn from captopril resumed normal control responding (indistinguishable from that of vehicle control animals) and the anxiolytic activity of SQ 29,852 was still present at 24 hours. This activity of SQ 29,852 waned to normal control values after 48 hours and subsequent measures showed there was no rebound anxiogenesis. The anxiolytic activity of fosinopril was lost on long-term treatment and behavior remained at control levels even on drug withdrawal. In contrast, the anxiolytic potential of zofenopril, lost on sub-chronic treatment, was regained on withdrawal. This anxiolytic activity waned over the 96 hours following withdrawal and anxiogenesis was never observed (animal behavior followed for up to 10 days after withdrawal) (FIGS. 15 and 16).

The above test results clearly show that ACE inhibitors have anti-anxiety activity and they are useful in reducing anxiety.

EXAMPLE 24

Antagonism of Anxiogenesis of Withdrawal from Subchronic treatment with Nicotine The same test procedure as described in Example 23 was used in a dependency study wherein an ACE inhibitor was administered to a test animal to reduce anxiety and thus facilitate withdrawal from nicotine dependency.

Methods

The studies used mice and the black:white test box system described in Example 23. Anxiolysis was measured as reduced aversion for the white, brightly-lit compartment (increased rearings and line crossings in the white, with corresponding reductions in the black, delayed latency to move out of the white and reduced % time spent in the black) and anxiogenesis as increased aversion for the white, brightly-lit area (decreased rearings and line crossings in the white, markedly increased in the black, rapid movement out of the white environment and increased time in the black environment).

Figure 17:
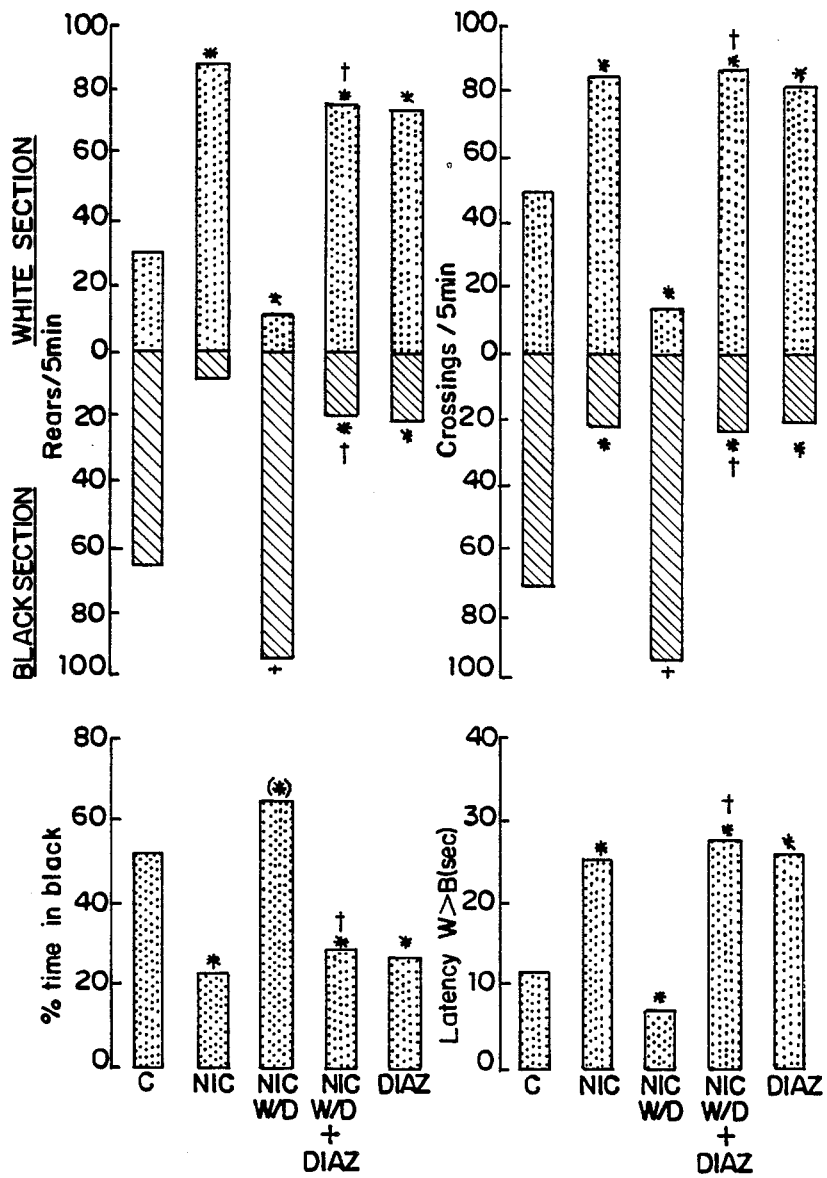
FIGS. 17, 18, 19, 20 and 21 show anxiolytic action of nicotine during intake, anxiogenesis of withdrawal and antagonism of withdrawal anxiogenesis by diazepam. n=5. S.E.M.s shown less than 12.9%. [*]P<0.05, *P<0.01 -P<0.001 (comparison with C) +P<0.001 (reversal withdrawal anxiogenesis); diazepam FIG. 17, captopril FIG. 18, SQ 29,852 FIG. 19, fosinopril FIG. 20, and zofenopril FIG. 21.
Figure 18:
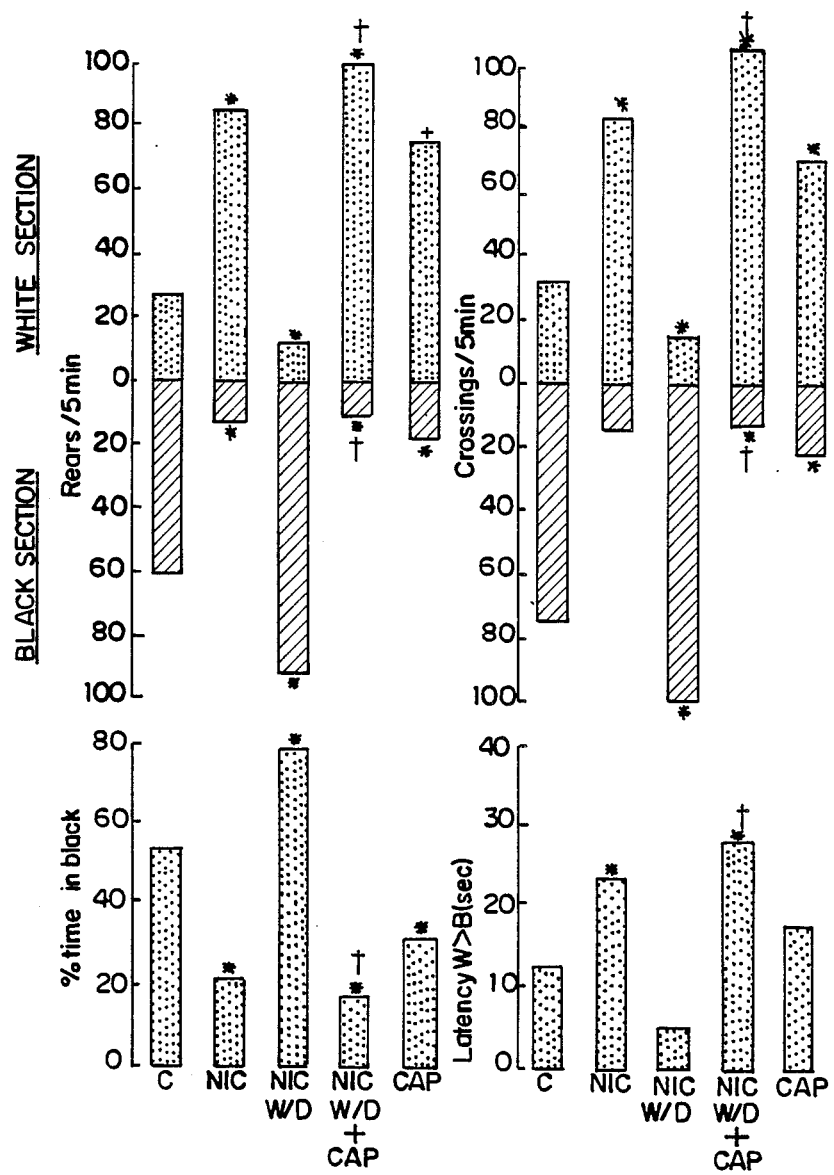
Figure 19:
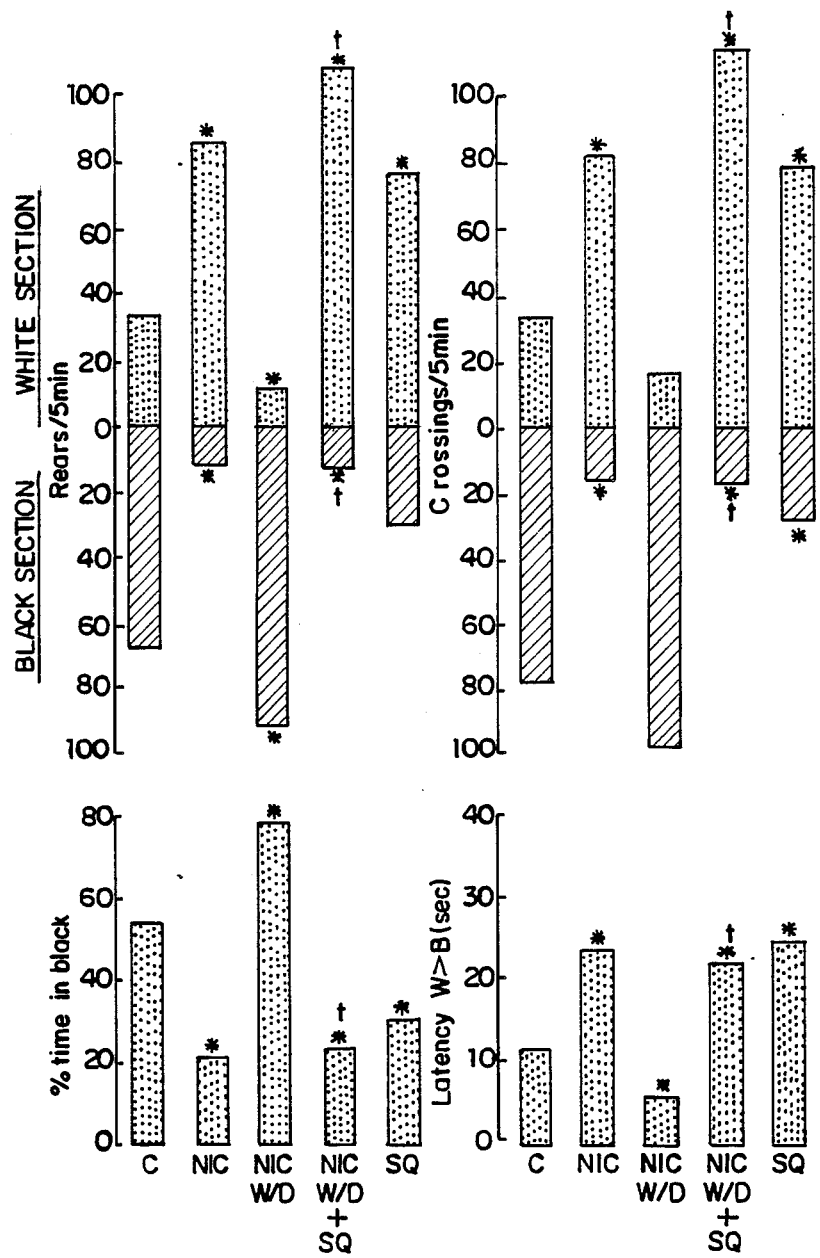
Figure 20:
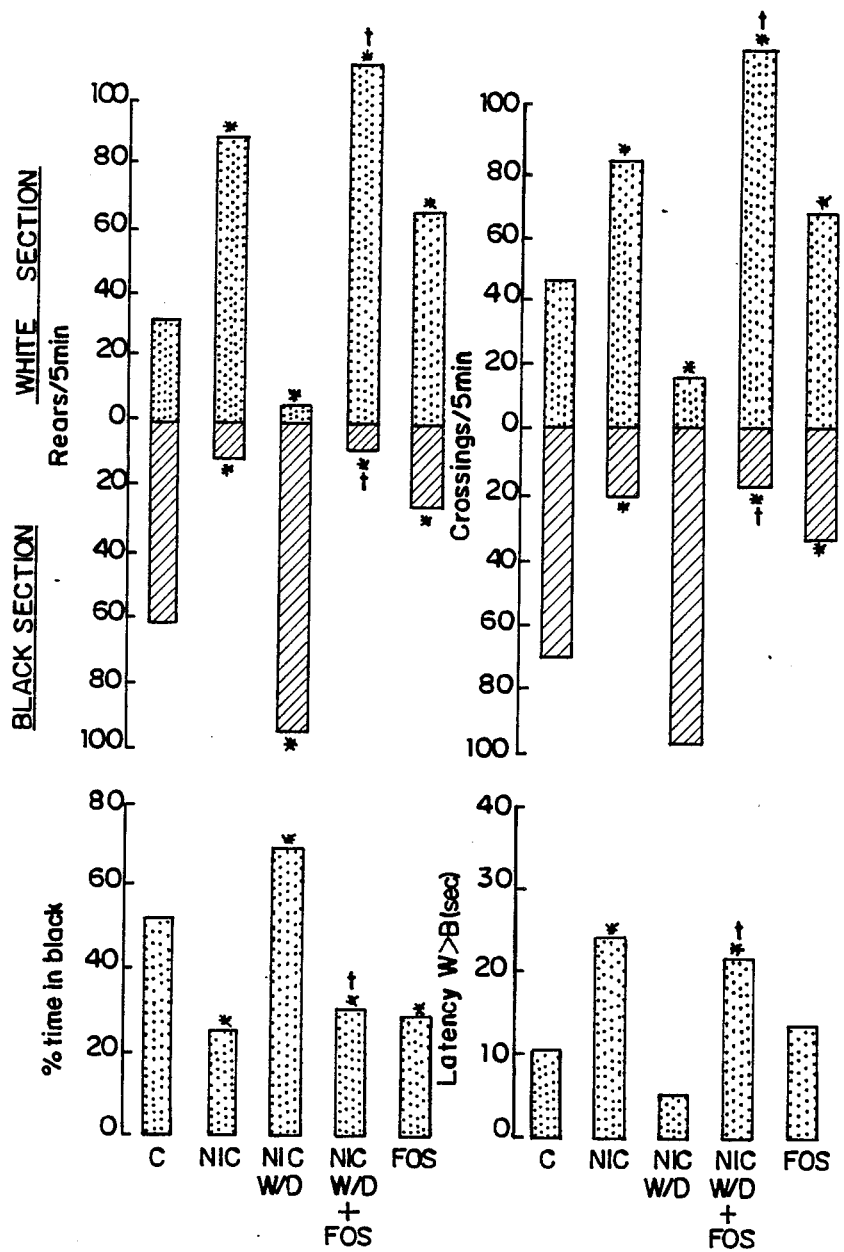
Figure 21:
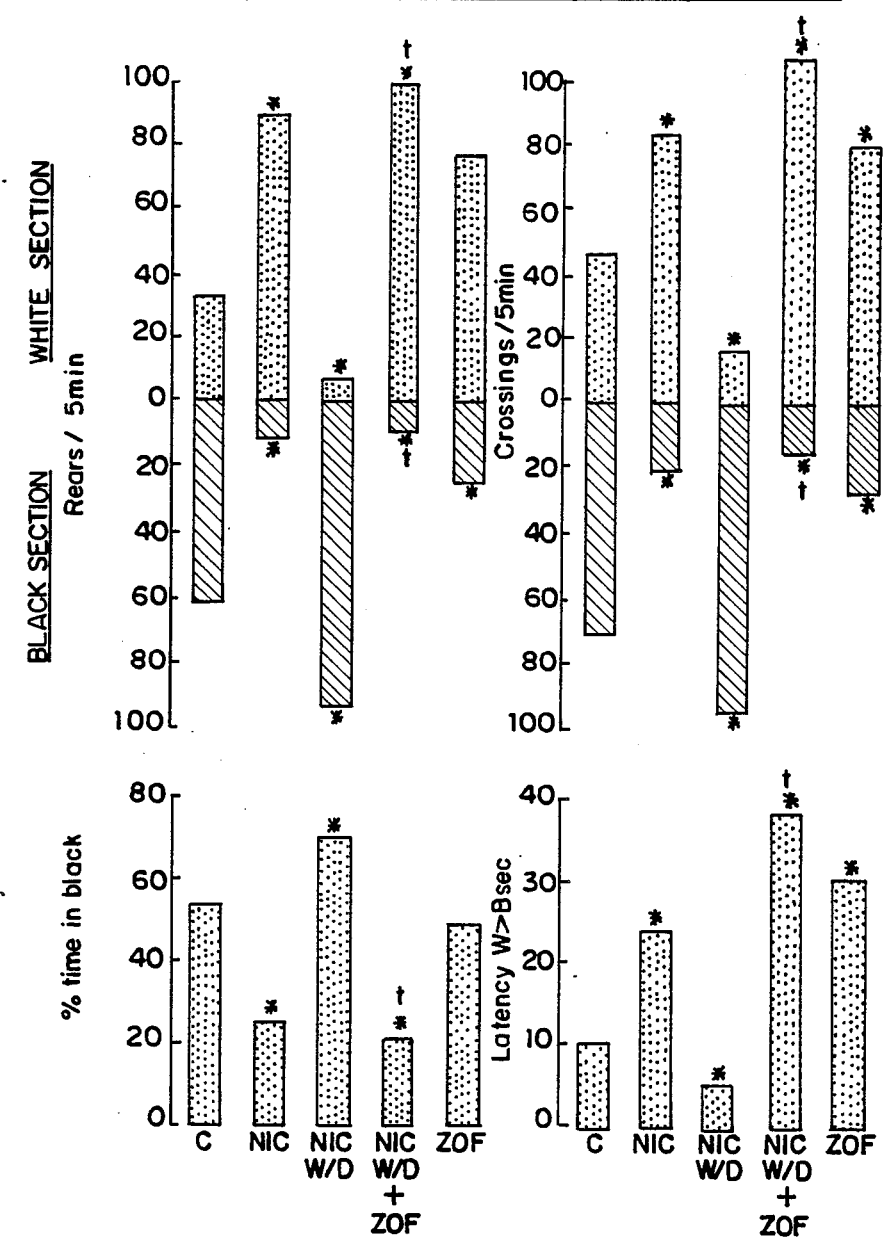

Nicotine was given at a dose of 0.1 mg/kg i.p. b.d. for 7 days (a dose carefully selected from extensive preliminary studies) (tested day 5 of treatment) and withdrawn for 24 hours (time of maximum anxiogenesis, again established from extensive preliminary studies). In FIG. 17, diazepam, 1.0 mg/kg i.p. b.d. (3 doses) was used as the positive control. In FIG. 18, captopril, 10 mg/kg i.p. b.d. (3 doses) was used as the positive control. In FIG. 19, SQ 29,852, 1 mg/kg i.p. b.d. (3 doses) was used as the positive control. In FIG. 20, fosinopril, 0.5 mg/kg i.p. b.d. (3 doses) was used as the positive control. In FIG. 21, zofenopril, 1.0 mg/kg i.p. b.d. (3 doses) was used as the positive control.

Results

Mice exhibit an anxiolysis during treatment with nicotine and an anxiogenesis on withdrawal. The anxiogenesis of withdrawal can be antagonized by diazepam, 1.0 mg/kg i.p. given at the time of nicotine withdrawal and then b.d. (3 doses, last dose given 45 minutes before test) (FIG. 17). The same profile of behavioral change was seen in experiments using captopril (10 mg/kg given at time of nicotine withdrawal and then b.d. (3 doses, last dose 60 minutes before test)), SQ 29,852 (1 mg/kg given at time of nicotine withdrawal and then b.d. (3 doses, last dose 60 minutes before test)), fosinopril (0.5 mg/kg given at time of nicotine withdrawal and then b.d. (3 doses, last dose 60 minutes before test)) and zofenopril (1 mg/kg given at time of nicotine withdrawal and then b.d. (3 doses, last dose 60 minutes before test)). Thus, in each experiment anxiolysis was seen during treatment with nicotine, anxiogenesis followed withdrawal from the subchronic nicotine treatment, and the withdrawal anxiogenesis was antagonized by captopril (10 mg/kg b.d.), SQ 29,852 (1.0 mg/kg b.d.), fosinopril (0.5 mg/kg b.d.) and zofenopril (1.0 mg/kg b.d.): in each situation the anxiogenesis of withdrawal was converted to an anxiolysis. This marked change in response from anxiogenesis to anxiolysis was also seen for diazepam (see FIGS. 17, 18, 19, 20 and 21). n=5 in all Figures.

In FIG. 17, S.E.M.'s shown less than 12.9%. [*]$P<0.05$, *$P<0.01$–$P<0.001$ (comparison with C (Control)) +$P<0.001$ (reversal withdrawal anxiogenesis).

In FIG. 18, S.E.M.'s shown less than 12.3%. *$P<0.001$ (comparison with C) +$P<0.001$ (reversal withdrawal anxiogenesis).

In FIG. 19, S.E.M.'s shown less than 11.7%. *$P<0.001$ (comparison with C). +$P<0.001$ (reversal withdrawal).

In FIG. 20, S.E.M.'s shown less than 12.6%. *$P<0.01$–$P<0.001$ (comparison with C) +$P<0.001$ (reversal withdrawal anxiogenesis).

In FIG. 21, S.E.M.'s shown less than 12.2%. *$P<0.001$ (comparison with C) +$P<0.001$ (reversal withdrawal anxiogenesis).

EXAMPLE 25

Antagonism of Anxiogenesis of Withdrawal from Subchronic Treatment with Alcohol Methods The same test procedure as described in Example 23 was used in a dependency study wherein an ACE inhibitor was administered to a test animal to reduce anxiety and thus facilitate withdrawal from alcohol dependency.

The studies used mice and the black:white test box system described in Example 23. Anxiolysis was measured as reduced aversion for the white, brightly-lit compartment (increased rearings and line crossings in the white, with corresponding reductions in the black, delayed latency to move out of the white and reduced % time spent in the black) and anxiogenesis as increased aversion for the white, brightly-lit area (decreased rearings and line crossings in the white, markedly increased in the black, rapid movement out of the white environment and increased time in the black environment).

Alcohol was presented in the drinking water (no choice) at a concentration of 8% w/v for 7 days (tested day 5 of treatment, also 24 hours after withdrawal). Extensive studies showed this approach to be acceptable (free choice situation and mice take 2% w/v alcohol), to cause anxiolysis during treatment and anxiogenesis within 24 hours of withdrawal. Antagonists were given at time of withdrawal and then b.d. (3 doses). Captopril (10 mg/kg i.p. b.d.), SQ 29,852 (1.0 mg/kg i.p. b.d.), fosinopril (0.5 mg/kg i.p. b.d.), zofenopril (1.0 mg/kg i.p. b.d.) and diazepam (1.0 mg/kg i.p. b.d.) were used as positive controls.

Results

Figure 22:
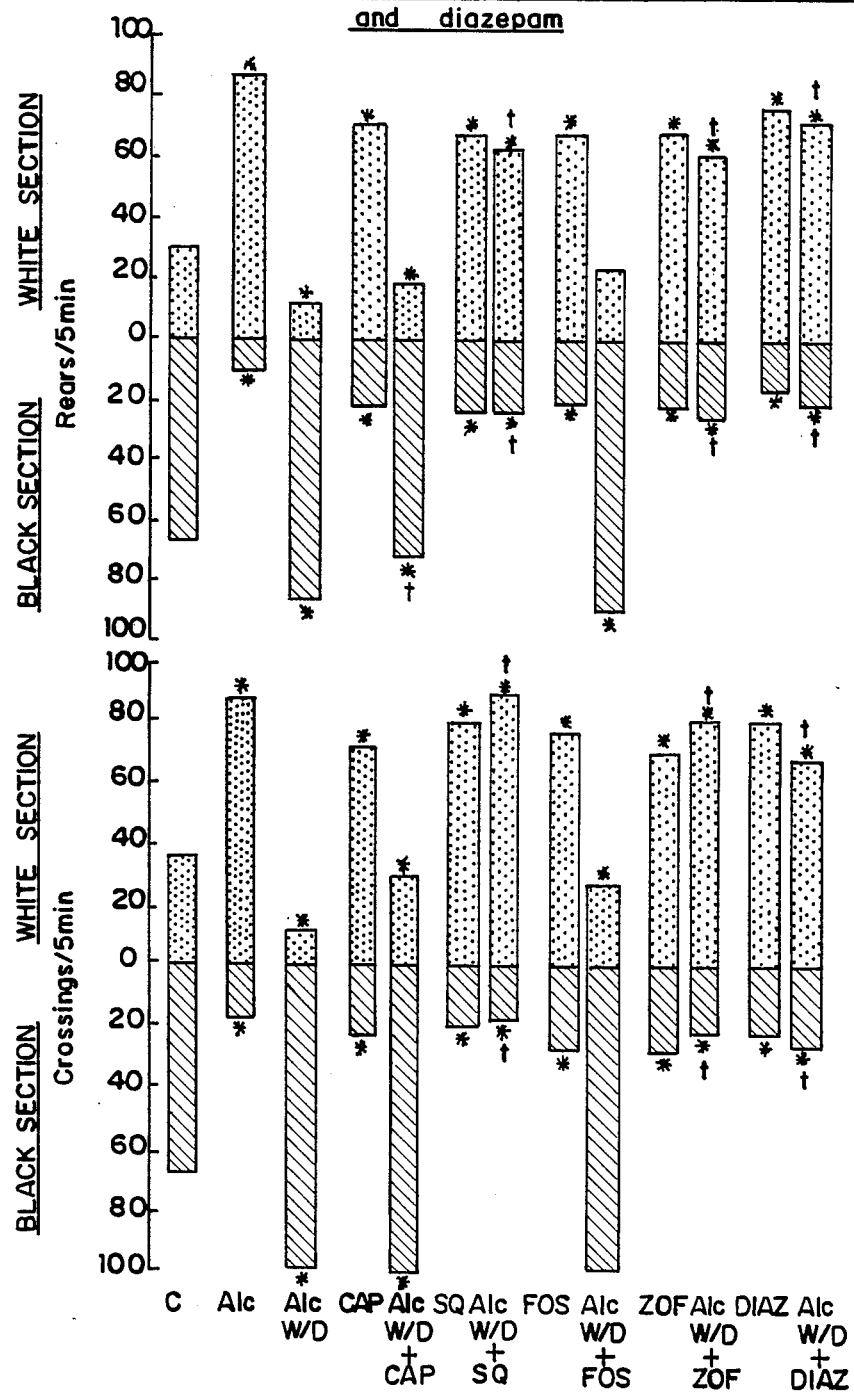
FIGS. 22 and 23 show anxiolytic action of alcohol during intake, anxiogenesis of withdrawal and antagonism of withdrawal anxiogenesis by SQ 29,852, zofenopril and diazepam.
Figure 23:
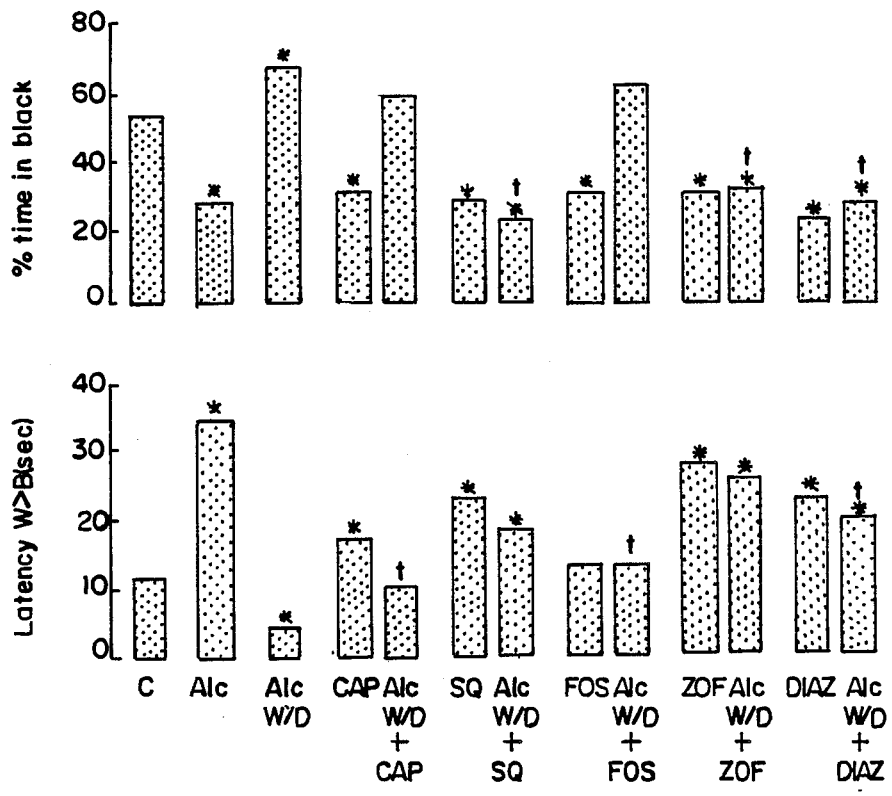

Mice exhibited anxiolysis during intake of alcohol (measured on day 5) and a marked anxiogenesis 24 hours after withdrawal of 7 days alcohol intake. The anxiogenesis of alcohol withdrawal was not antagonized by captopril (10 mg/kg i.p. b.d.) or by fosinopril (0.5 mg/kg i.p. b.d.) but was antagonized by SQ 29,852 (1.0 mg/kg i.p. b.d.), zofenopril (1.0 mg/kg i.p. b.d.) and by diazepam (1.0 mg/kg i.p. b.d.) (FIGS. 22 and 23). In FIGS. 22 and 23 n=5. In FIG. 22, S.E.M.'s shown less than 11.6%. *$P<0.05$-$P<0.001$ (comparison with C) +$P<0.01$-$P<0.001$ (reversal withdrawal). In FIG. 23, S.E.M.'s shown less than 12%. *$P<0.05$-$P<0.001$ (comparison with C) +$P<0.01$-$P<0.001$ (reversal withdrawal).

EXAMPLE 26

Antagonism of Anxiogenesis of Withdrawal from Subchronic Treatment with Diazepam Method The same test procedure as described in Example 23 was used in a dependency study wherein an ACE inhibitor was administered to a test animal to reduce anxiety and thus facilitate withdrawal from diazepam dependency.

The studies used mice and the black:white test box system described in Example 23. Anxiolysis was measured as reduced aversion for the white, brightly-lit compartment (increased rearings and line crossings in the white, with corresponding reductions in the black, delayed latency to move out of the white and reduced % time spent in the black) and anxiogenesis as increased aversion for the white, brightly-lit area (decreased rearings and line crossings in the white, markedly increased in the black, rapid movement out of the white environment and increased time in the black environment).

Figure 24:
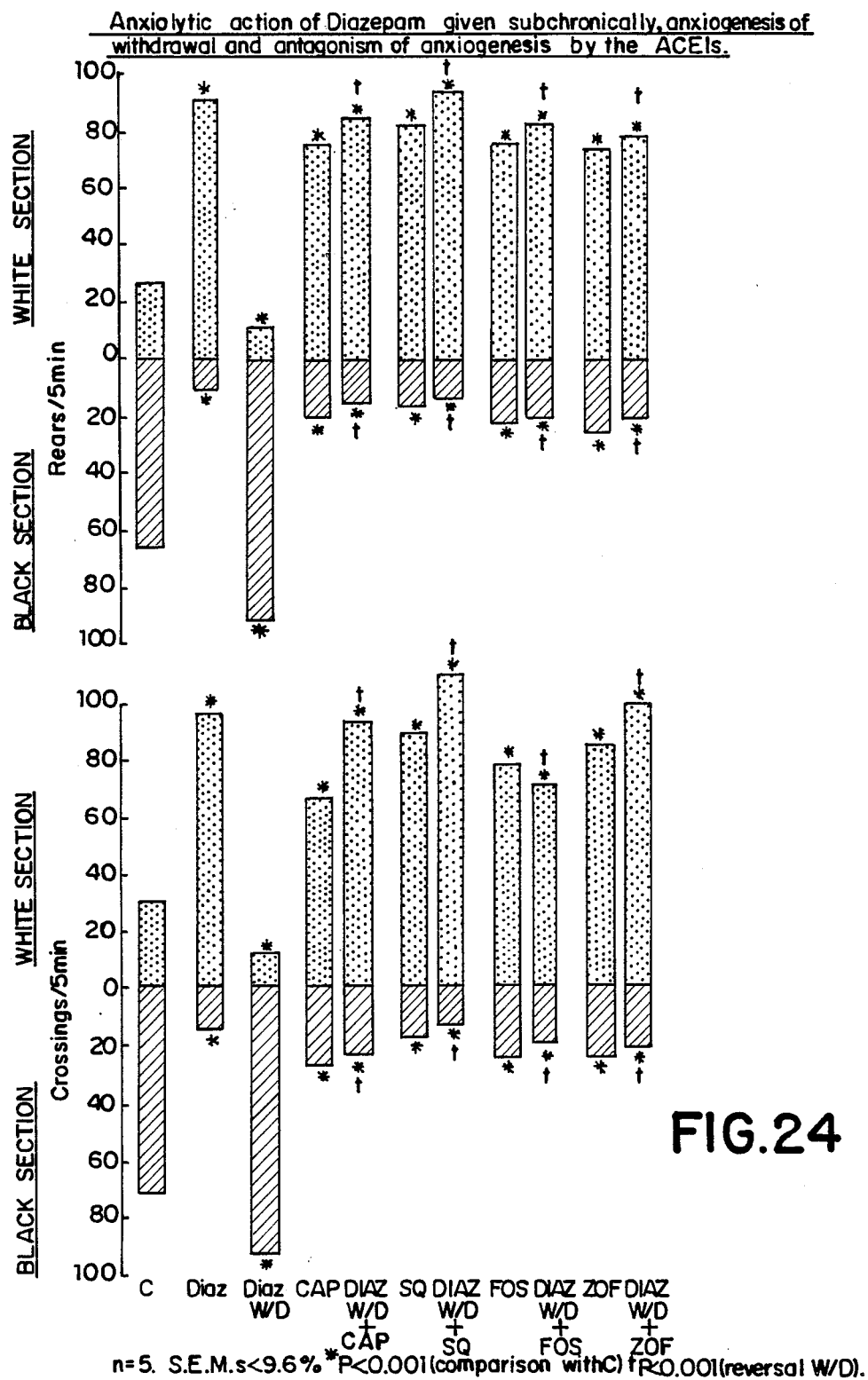
FIGS. 24 and 25 show anxiolytic action of diazepam given subchronically, anxiogenesis of withdrawal and antagonism of anxiogenesis by the ACE inhibitors.
Figure 25:
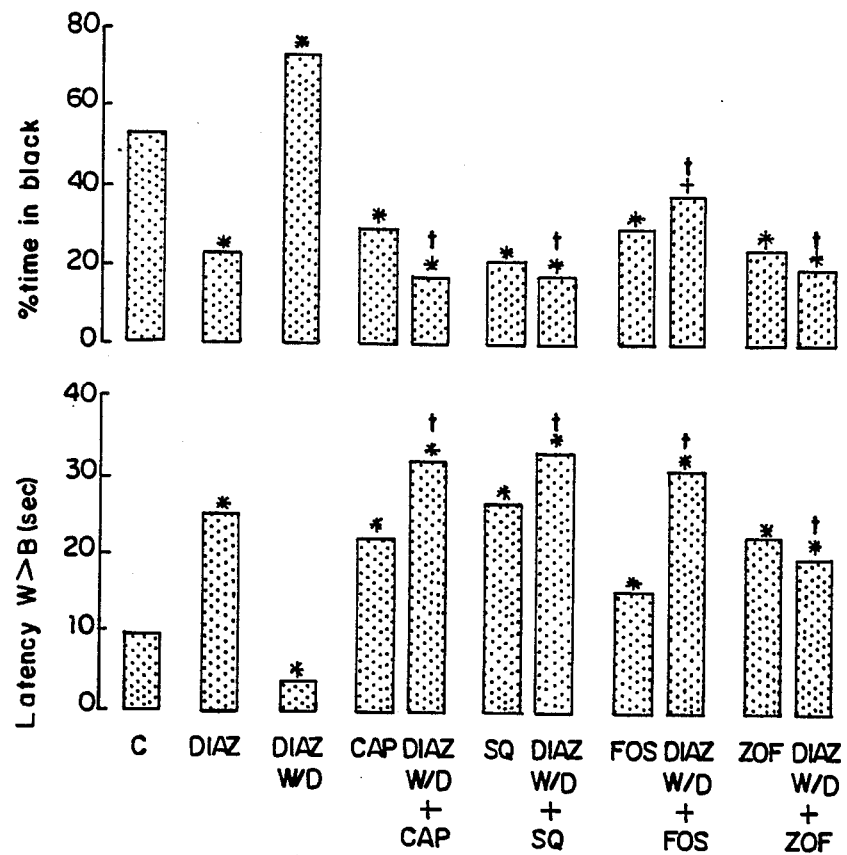

Diazepam was administered at a dose of 10 mg/kg i.p. b.d. for 7 days. Tolerance to sedation developed within 3 days and a full anxiolytic response was measured by day 5 (FIGS. 24 and 25). Within 8 hours of ceasing treatment with diazepam an anxiogenesis was developed, and this was marked 24 hours after withdrawal (FIGS. 24 and 25). The effects of potential antagonists were assessed 24 hours after withdrawal of diazepam treatment. Antagonists were given at time of withdrawal and then b.d. (3 doses). Captopril (10 mg/kg i.p. b.d.), SQ 29,852 (1 mg/kg i.p. b.d.), fosinopril (0.5 mg/kg i.p. b.d.), zofenopril (1 mg/kg i.p. b.d.) and diazepam (10 mg/kg i.p. b.d.) were used as positive controls.

Results

The anxiogenesis of withdrawal from diazepam was antagonized by captopril (10 mg/kg i.p. b.d.), SQ 29,852 (1.0 mg/kg i.p. b.d.), fosinopril (0.5 mg/kg i.p. b.d.) and zofenopril (1.0 mg/kg i.p. b.d.). Indeed, in each situation the anxiogenesis was converted to a full anxiolysis (FIGS. 24 and 25). In FIGS. 24 and 25, n=5 S.E.M.'s shown are less than 9.6% (FIG. 24) and less than 10.1% (FIG. 25) *$P<0.001$ (comparison with C) +$P<0.001$ (reversal withdrawal).

EXAMPLE 27

The same test procedure as described in Example 23 was used in a dependency study wherein an ACE inhibitor was administered to a test animal to reduce anxiety and thus facilitate withdrawal from β-carboline dependency.

Vehicle treated controls were run on each day of testing. All agents were given by the intraperitoneal routes using 30-60 minutes pretreatment times as defined in the figure legends. Anxiogenesis was induced by the β-carboline FG7142 at 1 mg/kg i.p. 30 minutes. The following agents were administered as positive controls and to determine their potential to antagonize the anxiogenesis caused by FG7142: diazepam, captopril, epicaptopril, SQ 29,852, fosinopril and zofenopril.

Results

Figure 27:
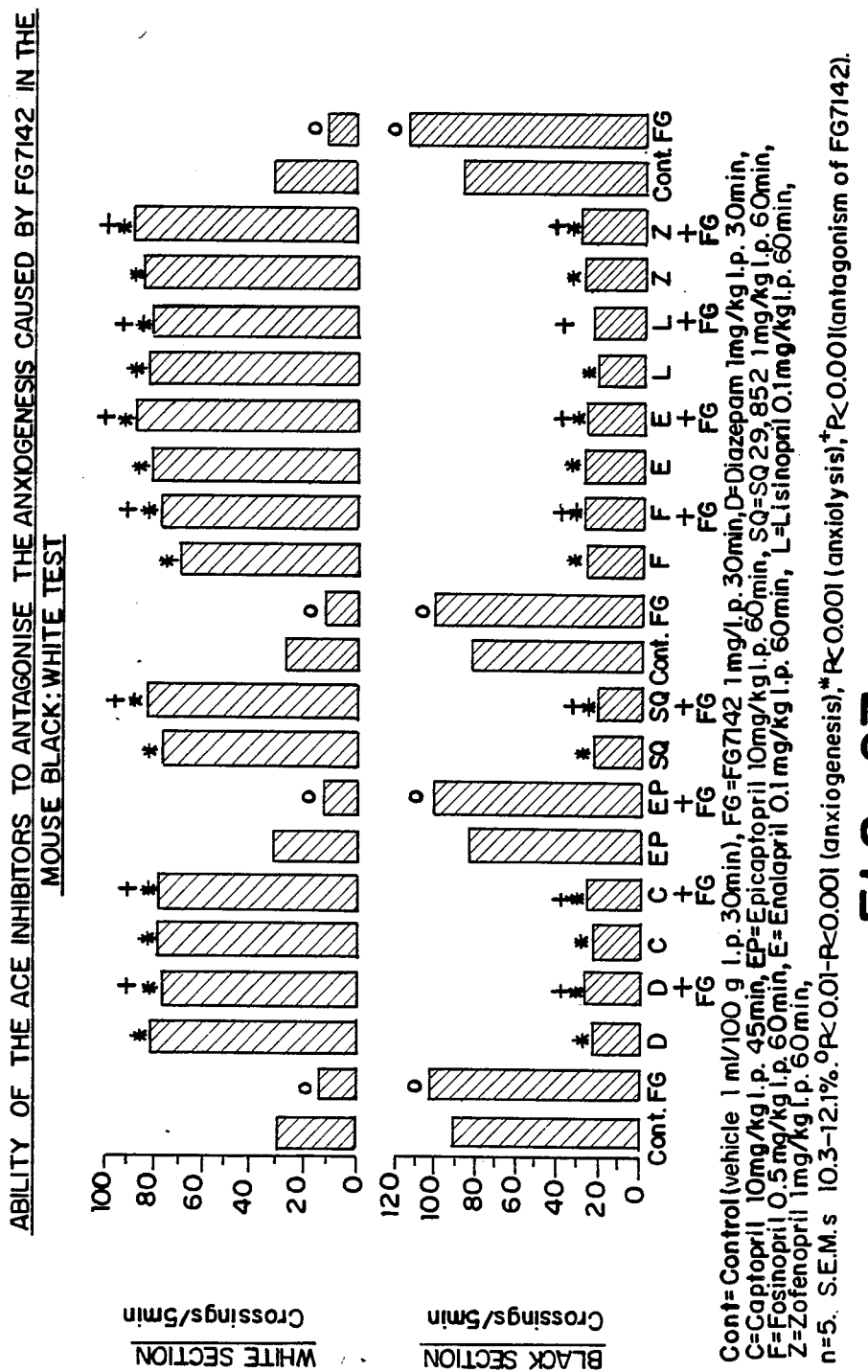
Figure 28:
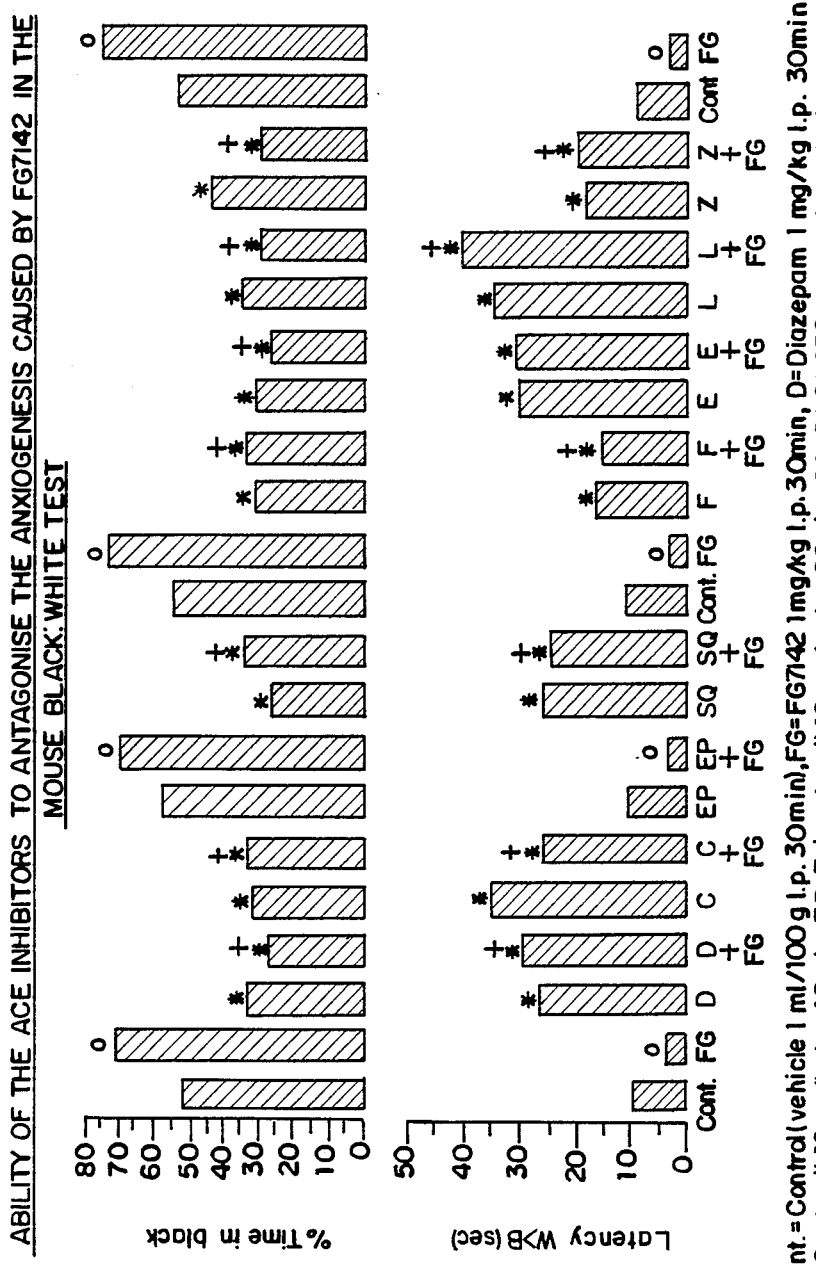

Treatment with 1 mg/kg i.p. 30 minutes FG7142 caused an anxiogenesis as characterized in the black:white test box as decreased rearings in the white with increases in the black (FIG. 26), decreased line crossings in the white with corresponding increases in the black (FIG. 27), increased % time in the black (FIG. 28) and reduced latency to move from the white to the black compartment of the test box (FIG. 28).

Figure 26:
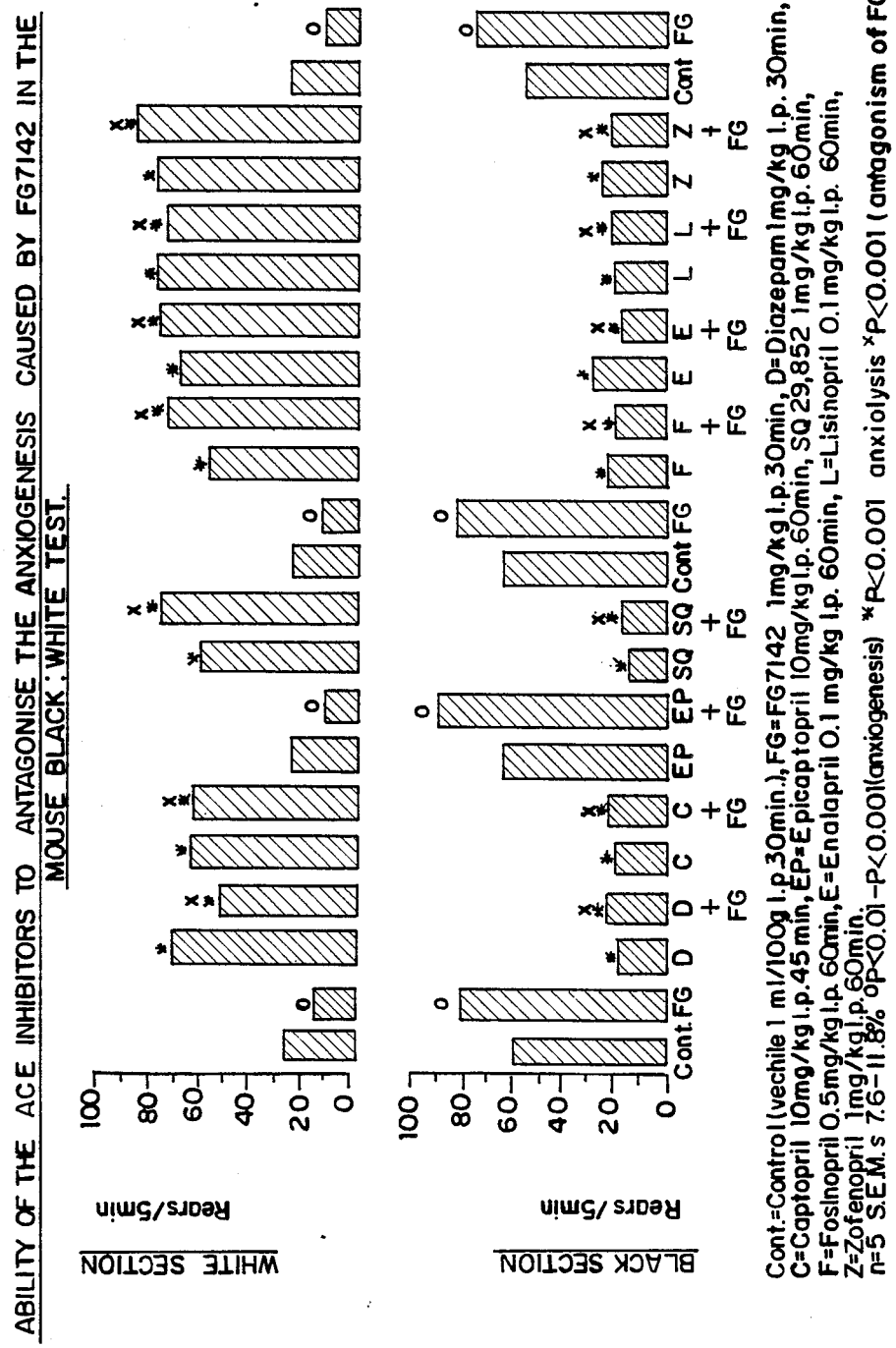
FIGS. 26, 27 and 28 show ability of ACE inhibitors to antagonize the anxiogenesis caused by FG7142 in the mouse black:white test.

These anxiogenic effects of FG7142 were antagonized by diazepam (1 mg/kg i.p. 30 minutes), captopril (10 mg/kg i.p. 45 minutes), SQ 29,852 (1 mg/kg i.p. 60 minutes), fosinopril (0.5 mg/kg i.p. 60 minutes), enalapril (0.1 mg/kg i.p. 60 minutes), lisinopril (0.1 mg/kg i.p. 60 minutes) and zofenopril (1 mg/kg i.p. 60 minutes (FIGS. 26, 27 and 28). Epicaptopril (10 mg/kg i.p. 60 minutes) and Control (vehicle 1 ml/100 g i.p. 30 minutes) failed to influence the anxiogenesis caused by FG7142 (FIGS. 26, 27 and 28). The experiments carried out and shown on FIGS. 26, 27 and 28 were carried out on 3 separate occasions and therefore 3 sets of comparative control (vehicle) and FG7142 data are given.

Conclusion

The ACE inhibitors, like diazepam, are able to antagonize the anxiogenesis caused by the β-carboline FG7142. Epicaptopril was without effect to confirm the specificity of the ACE inhibitor response. n=5 in each of FIGS. 26, 27 and 28. S.E.M.'s shown are less than 7.6-11.8% (FIG. 26), less than 10.3-12.1% (FIG. 27) and less than 9.4-12.7% (FIG. 28). °$P<0.1$-$P<0.001$ (anxiogenesis), *P<0.001 (anxiolysis), +P<0.001 (antagonism of FG7142).

EXAMPLE 28

Test of Anxiolytic Potential Using the Rat Social Interaction Test Methods

Male Sprague-Dawley rats, 225-275 g, were normally housed in groups of 5 and kept on a 12 hour light/dark cycle with lights on at 08.00 hour. Tests were conducted between 13.00-18.00 hours in an illuminated room. The apparatus used for the detection of changes in rat social interaction and exploratory behavior consisted of an opaque white Perspex open-topped box (45×32 cm and 20 cm high) with 15×16 cm areas marked on the floor. Two naive rats, from separate housing cages, were placed into the box (with a 100W bright white illumination 17 cm above) and their behavior observed over a 10 minute period by remote video recording. Two behaviors were noted, (a) social interaction between the animals was determined by timing (sec), sniffing of partner, crawling under or climbing over partner, genital investigation of partner, following partner and (b) exploratory locomotion was measured as the number of crossings of the lines marked on the floor of the test box. Values for time spent in social interaction and moving around the observation cage were determined for individual animals. Naive animals were used in drug treated pairs in treatment groups of 6. As with the mouse studies, data obtained was analyzed using single-factor Analysis of Variance followed by Dunnett's t test. Drugs were prepared as described for the mouse experiments. Pretreatment was for 45-60 minutes.

Results

Figure 29:
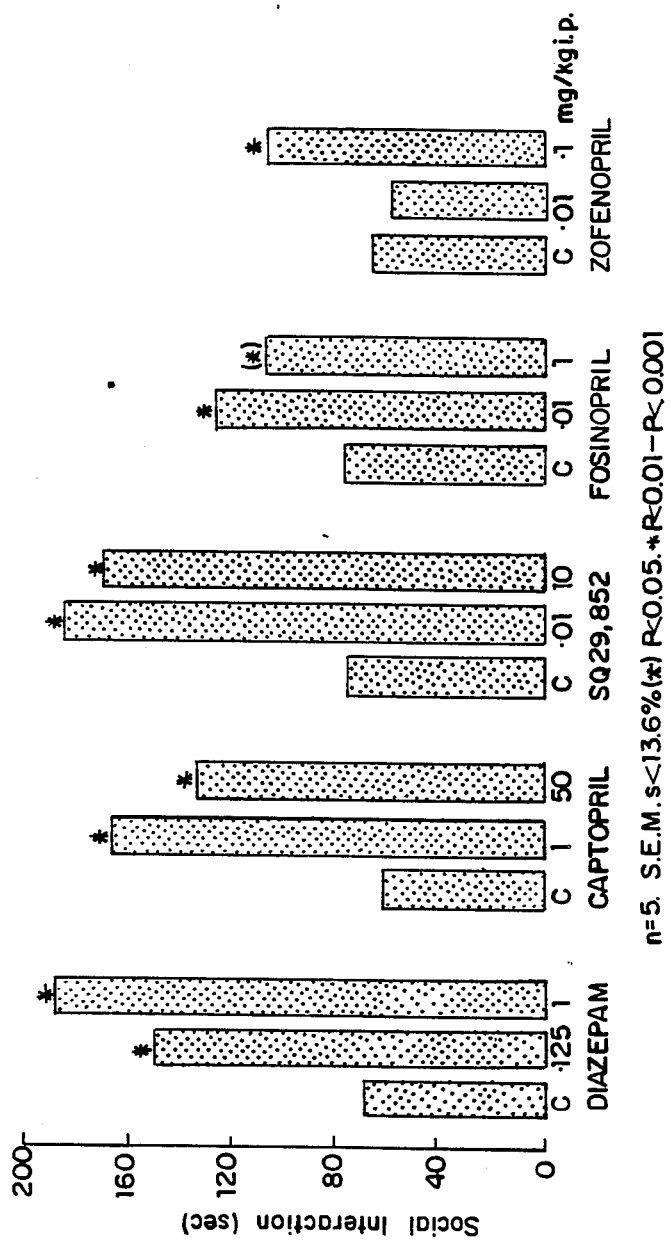
FIGS. 29 shows anxiolytic potential of ACE inhibitors seen on the rat social interaction test.

The anxiolytic action of diazepam was seen in the rat as increased social interaction (0.125-1 mg/kg i.p.). At doses above 1 mg/kg (2, 5 and 10 mg/kg i.p.) locomotor activity was suppressed. The marked increase in rat social interaction seen after diazepam treatment was also seen after administration of captopril (1-50 mg/kg i.p.) and SQ 29,852 (0.01-10 mg/kg i.p.). The activity of both of these compounds was maintained on oral administration (1-50 mg/kg p.o. captopril, 0.1-10 mg/kg p.o. SQ 29,852). Increased social interaction could also be seen following treatment with fosinopril (0.01 mg/kg, but loss of effect at 1 mg/kg) or zofenopril (0.1 mg/kg) although the intensity of response was less marked than for diazepam, captopril or SQ 29,852 (FIG. 29). n=5 S.E.M.'s shown less than 13.6% [*]P<0.05. *P<0.01-P<0.001.

EXAMPLE 29

Assessment of Anxiolytic Potential Using the Marmoset Human Threat Test

Male and female laboratory bred common marmosets (Callithrix jacchus) weighing between 350-400 g, were housed in single sex pairs. Holding rooms were maintained at 25°±1° C. at a humidity of 55% and on a 12 hour light/dark cycle (with simulated dawn and twilight periods, red illumination) with lights on at 07.00 hours. Tests were conducted between 13.30-15.30 hours in the normal holding room (to avoid unwanted disruption of behavior by movement to a novel room or cage). The holding cages measured 75 cm high, 50 cm wide and 60 cm deep. A behavioral change characterized by retreat from, and posturing towards a human threat (a behavior sensitive to known anxiolytic agents) was initiated by a human observer standing in close proximity in front of the holding cage. Changed behavior was recorded over a 2 minute period by the observer. The behavioral measures selected for the present study were, (a) the % of time spent on the cage front in direct confrontation with the human threat and (b) the number of body postures, primarily shown as raising of the tail to expose the genital region with varying degrees of body piloerection, anal scent marking and slit stare with flattened ear tufts.

12 marmosets were used at 7 day intervals throughout the study and were subject to a random cross-over of treatments. They were separated according to their basal anxiety responding. Statistical analysis utilized a one-way analysis of variance followed by Dunnett's t test. Drugs were prepared for the marmoset studies as described for the mouse (except that normal saline was used instead of distilled water). In the marmoset the route of administration was always subcutaneous (s.c.).

Results

Reduced anxiety is exhibited by marmosets as reduced numbers of postures exhibited in a fixed period and increased time on the cage front in direct confrontation with the human threat. This is clearly seen for diazepam in FIG. 30 with a dose-dependent effect between 10 and 25 μg/kg s.c. The first group of marmosets used to assess the potential anxiolytic actions of the ACE inhibitors had relatively low baseline anxiety responses. Nevertheless, the anxiolytic actions of diazepam (0.25 mg/kg s.c.), captopril (1.0 mg/kg s.c.) and SQ 29,852 (0.1 mg/kg s.c.) were clearly demonstrated as reduced posturing and, for diazepam and captopril, as increased time spent on the cage front (FIG. 31).

Figure 32:
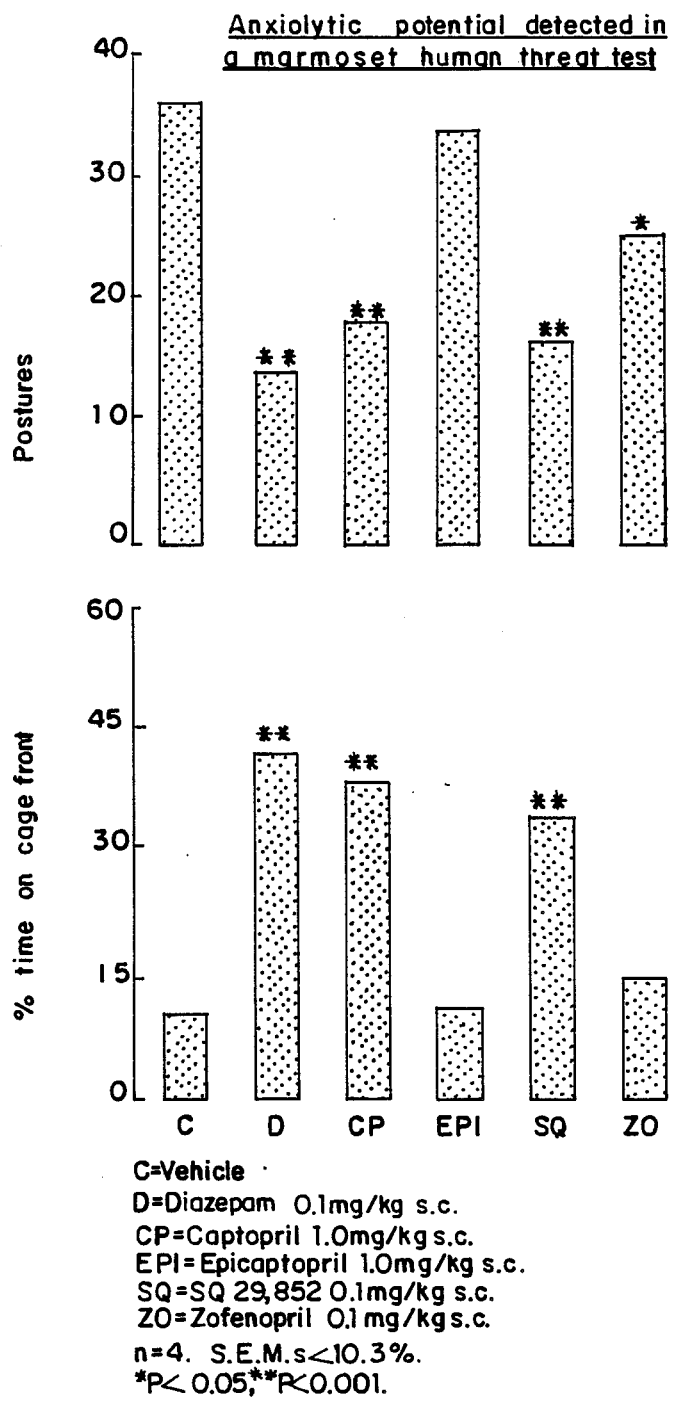

In a second group of marmosets the basal anxiety responding was higher (FIG. 32). In these animals diazepam (0.1 mg/kg s.c.), captopril (1.0 mg/kg s.c.) and zofenopril (0.1 mg/kg s.c.) were all shown to exert marked anxiolytic action, seen both as reduced posturing and (with the exception of zofenopril) increased time on the cage front. Of these compounds zofenopril was the least effective anxiolytic agent. However, in contrast to diazepam and the ACE inhibitors tested, epicaptopril was shown in the marmoset, as in the mouse, to be devoid of anxiolytic potential (FIG. 32).

Figure 30:
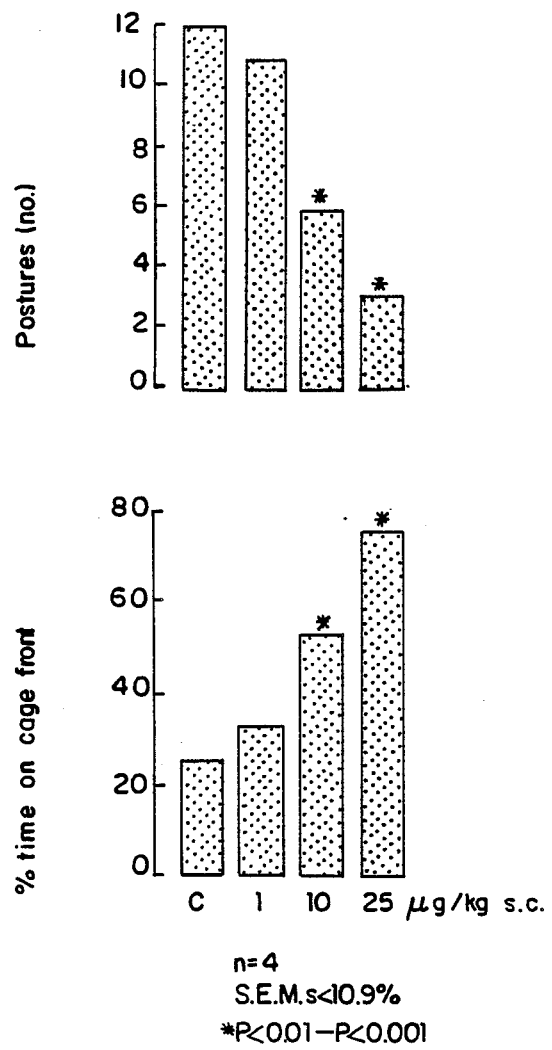

In FIGS. 30, 31 and 32, n=4. S.E.M.'s shown less than 10.9% *P<0.01-P<0.001 in FIG. 30, less than 11.7% *P<0.001 in FIG. 31 and less than 10.3% *P<0.05, **P<0.001 in FIG. 32.

What is claimed is:

1. A method for inhibiting onset of or treating anxiety in a mammalian specie, which comprises administering to a mammalian specie in need of such treatment an anxiolytic effective amount of an angiotensin converting enzyme inhibitor, alone or in combination with a calcium channel blocker.

2. The method as defined in claim 1 wherein the angiotensin converting enzyme inhibitor is a phosphonate substituted amino or imino acid or salt thereof, a proline derivative, a substituted proline derivative, a carboxyalkyl dipeptide derivative, a phosphinylalkanoyl proline derivative or a phosphonamidate derivative.

3. The method as defined in claim 1 wherein said angiotensin converting enzyme inhibitor is a proline derivative or a substituted proline derivative.

4. The method as defined in claim 1 wherein said angiotensin converting enzyme inhibitor is a carboxyalkyl dipeptide derivative.

5. The method as defined in claim 1 wherein said angiotensin converting enzyme inhibitor is a phosphinylalkanoyl proline derivative, a phosphoramidate derivative, or a phosphonate substituted amino or imino acid or salt thereof.

6. The method as defined in claim 1 wherein said angiotensin converting enzyme inhibitor is captopril.

7. The method as defined in claim 1 wherein said angiotensin converting enzyme inhibitor is enalapril.

8. The method as defined in claim 1 wherein said angiotensin converting enzyme inhibitor is lisinopril.

9. The method as defined in claim 1 wherein said angiotensin converting enzyme inhibitor is zofenopril.

10. The method as defined in claim 1 wherein said angiotensin converting enzyme inhibitor is fosinopril.

11. The method as defined in claim 1 wherein said angiotensin converting enzyme inhibitor is (S)-1-[6-amino-2-[[hydroxy(4-phenylbutyl)phosphinyl]oxy]-1-oxohexyl]-L-proline.

12. The method as defined in claim 1 wherein said angiotensin converting enzyme inhibitor is administered in single or divided doses of from about 0.1 to about 500 mg/one to four times daily and where present the calcium channel blocker is administered in single or divided doses of from about 1 to about 300 mg/1 to 4 times daily.

13. The method as defined in claim 1 wherein the angiotensin converting enzyme inhibitor is administered with a calcium channel blocker.

14. The method as defined in claim 13 wherein the calcium channel blocker is diltiazem, a 4-phenyl-1,4-dihydropyridine or verapamil.

15. The method as defined in claim 14 wherein the 4-phenyl-1,4-dihydropyridine is nifedipine or nitrendipine.

16. The method as defined in claim 13 wherein the angiotensin converting enzyme inhibitor is employed in a weight ratio to the calcium channel blocker of within the range of from about 0.1:1 to about 10:1.

17. A method for inhibiting onset of or treating anxiety in a mammalian specie associated with withdrawal from drugs of dependency and/or addiction, which comprises administering to a mammalian specie in need of such treatment an anxiolytic effective amount of an angiotensin converting enzyme inhibitor, alone or in combination with a calcium channel blocker.

18. The method as defined in claim 17 for reducing anxiety associated with nicotine withdrawal, alcohol withdrawal, diazepam withdrawal or cocaine withdrawal.

19. The method as defined in claim 17 for reducing anxiety and thus facilitating withdrawal from nicotine, alcohol, diazepam or cocaine.

20. The method as defined in claim 17 for reducing anxiety associated with nicotine withdrawal wherein the angiotensin converting enzyme inhibitor administered is captopril, SQ 29,852, fosinopril, zofenopril, enalapril or lisinopril.

21. The method as defined in claim 17 for reducing anxiety associated with alcohol withdrawal wherein the angiotensin converting enzyme inhibitor administered is SQ 29,852, zofenopril, enalapril or lisinopril.

22. The method as defined in claim 17 for reducing anxiety associated with diazepam withdrawal wherein the angiotensin converting enzyme inhibitor administered is captopril, SQ 29,852, fosinopril, zofenopril, enalapril or lisinopril.

23. A method for inhibiting onset of or treating anxiety in a mammalian specie, which comprises administering to a mammalian specie in need of such treatment an anxiolytic effective amount of an angiotensin converting enzyme inhibitor.

24. The method as defined in claim 23 wherein the angiotensin converting enzyme inhibitor is a phosphonate substituted amino or imino acid or salt thereof, a proline derivative, a substituted proline derivative, a carboxylalkyl dipeptide derivative, a phosphinylalkanoyl proline derivative or a phosphonamidate derivative.

25. The method as defined in claim 23 wherein said angiotensin converting enzyme inhibitor is captopril.

26. The method as defined in claim 23 wherein said angiotensin converting enzyme inhibitor is enalapril.

27. The method as defined in claim 23 wherein said angiotensin converting enzyme inhibitor is lisinopril.

28. The method as defined in claim 23 wherein said angiotensin converting enzyme inhibitor is zoafinopril.

29. The method as defined in claim 23 wherein said angiotensin converting enzyme inhibitor is fosinopril.

30. The method as defined in claim 23 wherein said angiotensin converting enzyme inhibitor is (S)-1-[6-amino-2-[[hydroxy(4-phenylbutyl)phosphinyl]oxy]-1oxohexyl]-L-proline.

31. A method for inhibiting onset of or treating anxiety in a mammalian specie associated with withdrawal from drugs of dependency and/or addiction, which comprises administering to a mammalian specie in need of such treatment an anxiolytic effective amount of an angiotensin converting enzyme inhibitor.

32. The method as defined in claim 31 for reducing anxiety associated with nicotine withdrawal, alcohol withdrawal, diazepam withdrawal or cocaine withdrawal.

33. The method as defined in claim 31 for reducing anxiety and thus facilitating withdrawal from nicotine, alcohol, diazepam or cocaine.

34. The method as defined in claim 31 for reducing anxiety associated with nicotine withdrawal wherein the angiotensin converting enzyme inhibitor administered is captopril, SQ 29,852, fosinopril, zofenopril, enalapril or lisinopril.

35. The method as defined in claim 31 for reducing anxiety associated with alcohol withdrawal wherein the angiotensin converting enzyme inhibitor administered is SQ 29,852, zofenopril, enalapril or lisinopril.

36. The method as defined in claim 31 for reducing anxiety associated with diazepam withdrawal wherein the angiotensin converting enzyme inhibitor administered is captopril, SQ 29,852, fosinopril, zofenopril, enalapril or lisinopril.

* * * * *